US008647630B2

(12) United States Patent
Tsukui et al.

(10) Patent No.: US 8,647,630 B2
(45) Date of Patent: *Feb. 11, 2014

(54) MITE ALLERGEN

(75) Inventors: Toshihiro Tsukui, Fukushima (JP); Hajime Tsujimoto, Tokyo (JP); Shigehiro Iwabuchi, Fukushima (JP)

(73) Assignee: Nippon Zenyaku Kogyo Co., Ltd., Fukushima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/230,448

(22) Filed: Sep. 12, 2011

(65) Prior Publication Data

US 2012/0289679 A1 Nov. 15, 2012

Related U.S. Application Data

(63) Continuation of application No. 11/547,850, filed as application No. PCT/JP2005/007191 on Apr. 7, 2005, now Pat. No. 8,075,898.

(30) Foreign Application Priority Data

Apr. 9, 2004 (JP) ................................ 2004-116089

(51) Int. Cl.
*A61K 38/00* (2006.01)
*A61K 39/00* (2006.01)
*A61K 39/35* (2006.01)
*A61K 39/36* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl.
USPC ..................... 424/185.1; 424/275.1; 530/300; 530/350

(58) Field of Classification Search
None
See application file for complete search history.

(56) References Cited

U.S. PATENT DOCUMENTS

| 5,314,991 | A | 5/1994 | Oka et al. |
| 5,876,722 | A | 3/1999 | Yuuki et al. |
| 5,958,415 | A | 9/1999 | Yuuki et al. |
| 6,060,057 | A | 5/2000 | Thomas et al. |
| 6,086,897 | A | 7/2000 | Thomas et al. |
| 7,101,664 | B2 | 9/2006 | Katinger et al. |
| 8,075,898 | B2 * | 12/2011 | Tsukui et al. ............ 424/185.1 |
| 2001/0014457 | A1 * | 8/2001 | Spindel et al. ............ 435/7.2 |
| 2008/0260759 | A1 * | 10/2008 | Tsukui et al. ............ 424/185.1 |
| 2010/0247568 | A1 | 9/2010 | Tsukui et al. |

FOREIGN PATENT DOCUMENTS

EP 0473111 3/1992

OTHER PUBLICATIONS

Schumann et al., "Characterization of House Dust Mite and Scabies Mite Allergens by Use of Canine Serum Antibodies", Am. J. Vet. Res., vol. 62, No. 9, pp. 1344-1348 (2001).
T. Tsukui et al., "Establishment of a Dog IgE Detection System Using a Recombinant Dog High-Affinity IgE Receptor α (FcεRIα) Chain", The 136th Meeting of the Japanese Society of Veterinary Science, HS-9, p. 202 (2003), accompanied by an English translation thereof.
K. Kurata et al., "Immunological Findings in 3 Dogs Clinically Diagnosed with Allergic Rhinitis", J. Vet. Med. Sci., vol. 66, No. 1, pp. 25-29 (2004).
C. McCall et al., "Characterization and Cloning of a Major High Molecular Weight House Dust Mite Allergen (Der F 15) for Dogs", Vet. Immunol. Immunopathol., vol. 78, pp. 231-247 (2001).
E. Weber et al., "Identification, Characterization, and Cloning of a Complementary DNA Encoding A 60-KD House Dust Mite Allergen (Der F 15) for Human Beings and Dogs", K. Allergy Clin. Immunol., vol. 112, No. 1, pp. 79-86 (2003).
Thomas et al., "Characterization and Immunobiology of House Dust Mite Allergens," International Archives of Allergy and Immunology, vol. 129, No. 1, pp. 1-18, (2002), XP009032860.
Masuda et al., "Positive Reactions to Common Allergens in 42 Atopic Dogs in Japan," Veterinary Immunology and Immunopathology, Amsterdam, NL, vol. 73, No. 2, pp. 193-204, (2000), XP001157518.
Lee et al., "Protein Sequence Analysis of a Novel 103-kDa Dermatophagoides Pteronyssinus Mite Allergen and Prevalence of Serum Immunoglobulin E Reactivity to rDer p 11 in Allergic Adult Patients," Clinical and Experimental Allergy: Journal of the British Society for Allergy and Clinical Immunology, vol. 34, No. 3, Mar. 2004, pp. 354-362, (2004), XP002463135.
Foster et al., "Comparison of Intradermal and Serum Testing for Allergen-specific IgE Using a Feepsilon RIalpha-based Assay in Atopic Dogs in the UK," Veterinary Immunology and Immunopathology, vol. 93, No. 1-2, pp. 51-60, May 30, 2003, (2003), XP002463136.
Ngo et al., 'Computation Complexity, Protein Structure Prediction, and the Levinthal Paradox'. The Protein Folding Problem and Tertiary Structure Prediction. Ed. K. Merz and S. Le Grand. Boston: Birkhauser, 1994. 491-495.

(Continued)

*Primary Examiner* — Nora Rooney
(74) *Attorney, Agent, or Firm* — Greenblum & Bernstein, P.L.C.

(57) ABSTRACT

A safe and efficient recombinant mite allergen is provided as a therapeutic agent or a diagnostic agent for mite allergic diseases, which contains no anaphylaxis-inducing impurities. The following recombinant protein (a) or (b) is provided:

(a) a protein comprising the amino acid sequence represented by SEQ ID NO: 2 or 35; or (b) a protein comprising an amino acid sequence derived from the amino acid sequence represented by SEQ ID NO: 2 or 35 by deletion, substitution, or addition of one or several amino acids and having mite allergen activity.

5 Claims, 15 Drawing Sheets

(56) References Cited

OTHER PUBLICATIONS

Blumenthal et al., 'Definition of an Allergen.' Allergens and Allergen Immunotherapy. Ed. R Lockey, S. Bukantz and J. Bousquet. New York: Marcel Decker, 2004. 37-50.

Skolnick et al. 'From genes to protein structure and function: novel applications of computation approaches in the genomic era.' Trends in Biotech. 18:34-39, 2000.

Attwood et al. 'The Babel of Bioinformatics.' Science. 290(5491):471-473, 2000.

* cited by examiner

M : Molecular marker (produced by BIO-RAD)
1 : Soluble fraction of *Escherichia coli* BL21 after induction with IPTG
2 : Purified dog FcεRIα chain fused to GST protein

Fig. 7-1

| | |
|---|---|
| gac gat gta tta aag cag act gag gag cct att aaa agt gcc cag gat<br>Asp Asp Val Leu Lys Gln Thr Glu Glu Pro Ile Lys Ser Ala Gln Asp<br>1                   5                  10              15 | 48 |
| gta ttg gaa aag ttg ccc gat tca gat ttg aaa gat gaa atc gca gaa<br>Val Leu Glu Lys Leu Pro Asp Ser Asp Leu Lys Asp Glu Ile Ala Glu<br>                20                  25                  30 | 96 |
| aaa ctg gca acc atg aag cat tac aaa cat aag tta gaa aat gca aaa<br>Lys Leu Ala Thr Met Lys His Tyr Lys His Lys Leu Glu Asn Ala Lys<br>           35                  40                  45 | 144 |
| aat cca atc aaa atc gcc cat ttt gaa ttg gaa ttg ttg aca atg ttc<br>Asn Pro Ile Lys Ile Ala His Phe Glu Leu Glu Leu Leu Thr Met Phe<br>50                    55                  60 | 192 |
| aaa aag ttc caa tca tta ttg aac gaa gct aat gaa att atc aaa tcc<br>Lys Lys Phe Gln Ser Leu Leu Asn Glu Ala Asn Glu Ile Ile Lys Ser<br>65                    70                  75                  80 | 240 |
| ttg aca acc aca aca acg gaa ccg aca acc cca act cct gaa cca aca<br>Leu Thr Thr Thr Thr Thr Glu Pro Thr Thr Pro Thr Pro Glu Pro Thr<br>                  85                  90                  95 | 288 |
| aca aca act cct gaa ccg act acc aaa acc ccc gaa ccg act acc aaa<br>Thr Thr Thr Pro Glu Pro Thr Thr Lys Thr Pro Glu Pro Thr Thr Lys<br>                  100               105              110 | 336 |
| aca ccg gaa cca aca aca cca act cct gaa ccg act acc aaa acc ccc<br>Thr Pro Glu Pro Thr Thr Pro Thr Pro Glu Pro Thr Thr Lys Thr Pro<br>            115               120              125 | 384 |
| gaa ccg act acc aaa aca ccg gaa cca aca aca cca act cca gaa ccg<br>Glu Pro Thr Thr Lys Thr Pro Glu Pro Thr Thr Pro Thr Pro Glu Pro<br>      130               135                  140 | 432 |
| act acc aaa aca ccg gaa cca aca aca cca act cct gaa ccg act acc<br>Thr Thr Lys Thr Pro Glu Pro Thr Thr Pro Thr Pro Glu Pro Thr Thr<br>145                 150               155              160 | 480 |
| aaa acc ccc gaa ccg act acc aaa aca cct gaa cca tcc acc cca act<br>Lys Thr Pro Glu Pro Thr Thr Lys Thr Pro Glu Pro Ser Thr Pro Thr<br>                  165               170              175 | 528 |

Fig. 7-2

| | |
|---|---|
| ccg gac cgc tac caa aac ccc cga ccg cta cca aaa cac cgg acc atc<br>Pro Asp Arg Tyr Gln Asn Pro Arg Pro Leu Pro Lys His Arg Thr Ile<br>              180                    185                  190 | 576 |
| cac ccc aac tcc gga ccg act acc aaa aca cct gaa cca tcc act cca<br>His Pro Asn Ser Gly Pro Thr Thr Lys Thr Pro Glu Pro Ser Thr Pro<br>              195                    200                  205 | 624 |
| act ccg gaa ccg act acc aaa acc ccc gaa ccg act acc aaa aca ccg<br>Thr Pro Glu Pro Thr Thr Lys Thr Pro Glu Pro Thr Thr Lys Thr Pro<br>210                    215                    220 | 672 |
| gaa cca tca acc cca act ccg gaa ccg act acc aaa aca ccg gaa cca<br>Glu Pro Ser Thr Pro Thr Pro Glu Pro Thr Thr Lys Thr Pro Glu Pro<br>225                    230                    235                  240 | 720 |
| tca acc cca act ccg gaa ccg act acc aaa aca ccg gaa cca tca acg<br>Ser Thr Pro Thr Pro Glu Pro Thr Thr Lys Thr Pro Glu Pro Ser Thr<br>              245                    250                  255 | 768 |
| act aag aaa cct aat cgg gat gat gtt ttg aaa caa gct gaa gag ctt<br>Thr Lys Lys Pro Asn Arg Asp Asp Val Leu Lys Gln Ala Glu Glu Leu<br>              260                    265                  270 | 816 |
| att aaa aga gcc gag gat gta ttt gaa aag ttg ccc gat tca gat ttg<br>Ile Lys Arg Ala Glu Asp Val Phe Glu Lys Leu Pro Asp Ser Asp Leu<br>              275                    280                  285 | 864 |
| aaa aat gaa atc gca gaa aaa ctg gca acc atg aag aat tac aaa cat<br>Lys Asn Glu Ile Ala Glu Lys Leu Ala Thr Met Lys Asn Tyr Lys His<br>              290                    295                  300 | 912 |
| gag tta gaa aat gca aaa aat cca atc aaa atc gcc cat ctt gaa tcg<br>Glu Leu Glu Asn Ala Lys Asn Pro Ile Lys Ile Ala His Leu Glu Ser<br>305                    310                    315                  320 | 960 |
| gaa ttg ttg aca atg ttc aaa atg ttc caa tca ttg tta aat gaa gcc<br>Glu Leu Leu Thr Met Phe Lys Met Phe Gln Ser Leu Leu Asn Glu Ala<br>                    325                    330                  335 | 1008 |
| aac gaa ctc ctg aa<br>Asn Glu Leu Leu<br>              340 | 1022 |

Fig. 8-1

| | |
|---|---:|
| atg aaa tta acc gct aca tta ctg ttg att cta aca ttg agt tgg gca<br>Met Lys Leu Thr Ala Thr Leu Leu Leu Ile Leu Thr Leu Ser Trp Ala<br>1                5                    10                15 | 48 |
| ggt att ttc gtt gat gca aat cca cga ttc aaa cgt gat aat cgg gat<br>Gly Ile Phe Val Asp Ala Asn Pro Arg Phe Lys Arg Asp Asn Arg Asp<br>                20                    25                    30 | 96 |
| gat gtt ttg aaa caa act gaa gag ctt att aaa agt gcc cag gat gta<br>Asp Val Leu Lys Gln Thr Glu Glu Leu Ile Lys Ser Ala Gln Asp Val<br>        35                    40                    45 | 144 |
| ttg gaa aag ttg ccc gat tca gat ttg aaa gat gaa atc gca gaa aaa<br>Leu Glu Lys Leu Pro Asp Ser Asp Leu Lys Asp Glu Ile Ala Glu Lys<br>        50                    55                    60 | 192 |
| ctg gca acc atg aag cat tac aaa cat aag tta gaa aat gca aaa aat<br>Leu Ala Thr Met Lys His Tyr Lys His Lys Leu Glu Asn Ala Lys Asn<br>65                    70                    75                    80 | 240 |
| cca atc aaa atc gcc cat ttt gaa ttg gaa ttg ttg aca atg ttc aaa<br>Pro Ile Lys Ile Ala His Phe Glu Leu Glu Leu Leu Thr Met Phe Lys<br>                      85                    90                    95 | 288 |
| aag ttc caa tca tta ttg aac gaa gct aat gaa att atc aaa tcc ttg<br>Lys Phe Gln Ser Leu Leu Asn Glu Ala Asn Glu Ile Ile Lys Ser Leu<br>                  100                  105                110 | 336 |
| aca acc aca aca acg gaa ccg aca acc cca act cct gaa cca aca aca<br>Thr Thr Thr Thr Thr Glu Pro Thr Thr Pro Thr Pro Glu Pro Thr Thr<br>                115                  120                125 | 384 |
| aca act cct gaa ccg act acc aaa acc ccc gaa ccg act acc aaa aca<br>Thr Thr Pro Glu Pro Thr Thr Lys Thr Pro Glu Pro Thr Thr Lys Thr<br>                130                  135                140 | 432 |

Fig. 8-2

| | |
|---|---|
| ccg gaa cca aca aca cca act cct gaa ccg act acc aaa acc ccc gaa<br>Pro Glu Pro Thr Thr Pro Thr Pro Glu Pro Thr Thr Lys Thr Pro Glu<br>145                      150                  155              160 | 480 |
| ccg act acc aaa aca ccg gaa cca aca aca cca act cca gaa ccg act<br>Pro Thr Thr Lys Thr Pro Glu Pro Thr Thr Pro Thr Pro Glu Pro Thr<br>             165                  170                  175 | 528 |
| acc aaa aca ccg gaa cca aca aca cca act cct gaa ccg act acc aaa<br>Thr Lys Thr Pro Glu Pro Thr Thr Pro Thr Pro Glu Pro Thr Thr Lys<br>        180                  185                  190 | 576 |
| acc ccc gaa ccg act acc aaa aca cct gaa cca tcc acc cca act ccg<br>Thr Pro Glu Pro Thr Thr Lys Thr Pro Glu Pro Ser Thr Pro Thr Pro<br>        195                  200                  205 | 624 |
| gac cgc tac caa aac ccc cga ccg cta cca aaa cac cgg acc atc cac<br>Asp Arg Tyr Gln Asn Pro Arg Pro Leu Pro Lys His Arg Thr Ile His<br>        210                  215                  220 | 672 |
| ccc aac tcc gga ccg act acc aaa aca cct gaa cca tcc act cca act<br>Pro Asn Ser Gly Pro Thr Thr Lys Thr Pro Glu Pro Ser Thr Pro Thr<br>225                      230                  235              240 | 720 |
| ccg gaa ccg act acc aaa acc ccc gaa ccg act acc aaa aca ccg gaa<br>Pro Glu Pro Thr Thr Lys Thr Pro Glu Pro Thr Thr Lys Thr Pro Glu<br>             245                  250                  255 | 768 |
| cca tca acc cca act ccg gaa ccg act acc aaa aca ccg gaa cca tca<br>Pro Ser Thr Pro Thr Pro Glu Pro Thr Thr Lys Thr Pro Glu Pro Ser<br>             260                  265                  270 | 816 |
| acc cca act ccg gaa ccg act acc aaa aca ccg gaa cca tca acg act<br>Thr Pro Thr Pro Glu Pro Thr Thr Lys Thr Pro Glu Pro Ser Thr Thr<br>             275                  280                  285 | 864 |

Fig. 8-3

```
aag aaa cct aat cgg gat gat gtt ttg aaa caa gct gaa gag ctt att      912
Lys Lys Pro Asn Arg Asp Asp Val Leu Lys Gln Ala Glu Glu Leu Ile
        290             295             300 aaa aga gcc gag gat gta ttt gaa aag ttg ccc gat tca gat ttg aaa      960
Lys Arg Ala Glu Asp Val Phe Glu Lys Leu Pro Asp Ser Asp Leu Lys
305             310             315             320 aat gaa atc gca gaa aaa ctg gca acc atg aag aat tac aaa cat gag     1008
Asn Glu Ile Ala Glu Lys Leu Ala Thr Met Lys Asn Tyr Lys His Glu
            325             330             335 tta gaa aat gca aaa aat cca atc aaa atc gcc cat ctt gaa tcg gaa     1056
Leu Glu Asn Ala Lys Asn Pro Ile Lys Ile Ala His Leu Glu Ser Glu
            340             345             350 ttg ttg aca atg ttc aaa atg ttc caa tca ttg ttg aac gaa gct gat     1104
Leu Leu Thr Met Phe Lys Met Phe Gln Ser Leu Leu Asn Glu Ala Asp
            355             360             365 gaa att atc aga tcc ttg aca act acg acg gaa ccg aca aca ttg aat     1152
Glu Ile Ile Arg Ser Leu Thr Thr Thr Thr Glu Pro Thr Thr Leu Asn
        370             375             380 agc acc act ccg gaa ccg aca aca ttg aat agc acc act ccg gaa ccg     1200
Ser Thr Thr Pro Glu Pro Thr Thr Leu Asn Ser Thr Thr Pro Glu Pro
385             390             395             400 aca aca ttg aat agc acc act ccg gaa ccg aca aca ttg aat agc acc     1248
Thr Thr Leu Asn Ser Thr Thr Pro Glu Pro Thr Thr Leu Asn Ser Thr
            405             410             415 act ccg gaa ccg aca aca ttg aat agc acc act ccg gga ccg aca aca     1296
Thr Pro Glu Pro Thr Thr Leu Asn Ser Thr Thr Pro Gly Pro Thr Thr
            420             425             430
```

Fig. 8-4

```
ttg aat agc acc act ccg gaa ccg aca aca ttg aat agc acc act ccg         1344
Leu Asn Ser Thr Thr Pro Glu Pro Thr Thr Leu Asn Ser Thr Thr Pro
        435             440             445 gaa ccg aca aca ttg aat agc acc act ccg gaa ccg aca aca tcg aat         1392
Glu Pro Thr Thr Leu Asn Ser Thr Thr Pro Glu Pro Thr Thr Ser Asn
        450             455             460 agc acc act tca gaa cca acg aat tca atc aat aga aaa aca agt gaa         1440
Ser Thr Thr Ser Glu Pro Thr Asn Ser Ile Asn Arg Lys Thr Ser Glu
465             470             475             480 ttt cat tct tat ccg att ggt tcc ata aga ttc gaa tca gat tca ata         1488
Phe His Ser Tyr Pro Ile Gly Ser Ile Arg Phe Glu Ser Asp Ser Ile
            485             490             495 ttt tct aaa cat ttt att ctt ttg att tga                                 1518
Phe Ser Lys His Phe Ile Leu Leu Ile Stop
            500             505
```

MITE ALLERGEN

This application is a Continuation of U.S. patent application Ser. No. 11/547,850, now U.S. Pat. No. 8,075,898 filed May 17, 2007, which is the National Stage of International Application No. PCT/JP05/07191, filed Apr. 7, 2005, which applications are considered as being a part of this application, and the entire disclosures of application Ser. Nos. 11/547,850 and PCT/JP05/07191 are expressly incorporated by reference herein in their entireties. This application also claims priority to Japanese Patent Application No. JP 2004-116089, filed Apr. 9, 2004.

TECHNICAL FIELD

The present invention relates to recombinant mite allergens having allergen activity and in particular relates to mite allergens that cause atopy in dogs. The present invention further relates to genes encoding the allergens, expression vectors that enable expression of the genes, transformants obtained by transformation using expression vectors, a method for producing the recombinant mite allergens, therapeutic agents for mite allergic diseases, and diagnostic agents for mite allergic diseases.

BACKGROUND ART

House dust mites are known as major causes of allergic diseases such as atopic dermatitis and bronchial asthma. Conventionally, desensitization therapy that uses causative substances of allergies as therapeutic agents for allergic diseases is regarded as the most important basic remedy. In particular, the desensitization therapy is broadly conducted for diseases such as pollinosis, house dust allergies, and fungal allergies, which are induced by antigens such as inhalant allergens that are difficult to avoid. However, the desensitization therapy involves the risk of anaphylaxis due to the action of sensitizing antigens, so that administration of safe sensitizing antigens is required. Such safe sensitizing antigens are under research.

Regarding mite allergic diseases, 2 types of mites, *Dermatophagoides pteronyssinus* and *Dermatophagoides farinae*, have been reported as allergen sources in house dust (see Non-patent documents 1 and 2). Major mite allergens have been fractionated from these mites. These mite allergens are known to be a glycoprotein (pI 4.6 to 7.2) with a molecular weight between 24 kD and 28 kD and/or a protein (pI 5 to 7.2) with a molecular weight between 14.5 kD and 20 kD contained in mite excretion and/or mite bodies (see Non-patent documents 3 to 7).

Regarding the mite allergen genes, Der p 1 (molecular weight: 25,371) and Der p 2 (molecular weight: 14,131) which are major allergens of *Dermatophagoides pteronyssinus* and Der f 1 (molecular weight: 25,191) and Der f 2 (molecular weight: 14,021) which are major allergens of *Dermatophagoides farinae* have been cloned and the nucleotide sequences thereof have also been determined (see Non-patent documents 8 to 15). Recombinant allergens based on these allergens have also been prepared, and research concerning the same has proceeded. Moreover, the nucleotide sequence of Der f 3, an allergen with a molecular weight of approximately 30,000, has also been reported (see Non-patent document 16). Furthermore, as mite allergens, ma 10, ma 3, ma 15, ma 29, ma 44, ma 50, ma 113, ma 114, and ma 115 (see Patent document 1) have also been reported. Moreover, ma 124, which exerts strong crossreactivity with an anti-Der f 2 serum, has also been reported (see Patent document 2).

Furthermore, it has been reported concerning dogs that 98-kDa Der f 15, 109-kDa Der f 15 (see Non-patent document 17), and 60-kDa Der f 18 (see Non-patent document 18) are allergens with which IgE strongly reacts.

As a method for diagnosing mite allergic diseases, an intradermal reaction test has conventionally been used as a mainstream method, which is based on a patient's history and uses house dust extracts and/or mite body extracts. This method (test) has been used in combination with a RAST (radio allergosorbent test) method that involves serum IgE antibody titer (relative value) measurement, an inhalation induction test, a nasal mucous membrane provocation test, and the like. However, it has remained considerably difficult to directly diagnose mite allergic diseases.

A desensitization therapeutic method for bronchial asthma has been conventionally performed, which uses a house dust extract and a house dust mite as a specific allergen. However, the composition of house dust has not been analyzed sufficiently. Moreover, house dust contains many types of impurities that can induce anaphylaxis. Hence, the doses of house dust in such cases are extremely limited. Accordingly, conventional desensitization treatment can have effects at extremely low levels. Therefore, more effective and safer antigens for desensitization treatment have been desired. It has been conventionally known that allergens effective for desensitization treatment are present in fractions of high-molecular-weight crude mite excretions. From such fractions, it has been impossible to obtain mite allergens in amounts sufficient for desensitization treatment. Therefore, with methods that involve extraction and purification of mite allergens from products obtained by raising mites, achieving a stable supply of antigens for treatment is difficult. Furthermore, as described above, various recombinant mite allergens have been conventionally reported with the use of gene recombination techniques. However, it cannot be said that these allergens are always effective for actual treatment. Provision of a recombinant mite allergen with more effective, new, and greater mite allergen activity has been desired.

Patent document 1 JP Patent Publication (Kokai) No. 7-112999 A (1995)
Patent document 2 JP Patent Publication (Kokai) No. 7-278190 A (1995)
Non-patent document 1 Allerg. Asthma, 10, 329-334 (1964)
Non-patent document 2 J. Allergy, 42, 14-28 (1968)
Non-patent document 3 J. Immunol., 125, 587-592 (1980)
Non-patent document 4 J. Allergy Clin. Immunol., 76, 753-761 (1985)
Non-patent document 5 Immunol., 46, 679-687 (1982)
Non-patent document 6 Int. Arch. Allergy Appl. Immunol., 81, 214-223 (1986)
Non-patent document 7 J. Allergy Clin. Immunol., 75, 686-692 (1985)
Non-patent document 8 Int. Arch. Allergy Appl. Immunol., 85, 127-129 (1988)
Non-patent document 9 J. Exp. Med., 167, 175-182 (1988)
Non-patent document 10 J. Exp. Med., 170, 1457-1462 (1989)
Non-patent document 11 Int. Arch. Allergy Appl. Immunol., 91, 118-123 (1990)
Non-patent document 12 Int. Arch. Allergy Appl. Immunol., 91, 124-129 (1990)
Non-patent document 13 Jpn. J. Allergol., 39, 557-561 (1990)
Non-patent document 14 Clinical and Experimental Allergy, 21, 25-32 (1991)
Non-patent document 15 Clinical and Experimental Allergy, 21, 33-37 (1991)
Non-patent document 16 FEBS Lett., 377, 62-66 (1995)

Non-patent document 17 Vet. Immunol. Immunopathol, 78, 231-247 (2001)

Non-patent document 18 J. Allergy Clin. Immunol, 112, 79-86 (2003)

DISCLOSURE OF THE INVENTION

An object of the present invention is to provide safe and effective recombinant mite allergens containing no anaphylaxis-inducing impurities as therapeutic agents or diagnostic agents for mite allergic diseases. More specifically, objects of the present invention are to provide genes derived from mite bodies and to provide expression vectors that enable expression of the genes. Still another object of the present invention is to provide novel mite allergens having allergen activity, which are obtained by expression of genes derived from mite bodies. Further objects of the present invention are to provide novel therapeutic agents for mite allergic diseases containing recombinant mite allergens as active ingredients and to provide novel diagnostic agents for mite allergic diseases containing recombinant mite allergens.

As a result of intensive studies to achieve the above objects, the present inventors have discovered novel mite allergens and also discovered that the allergens exert excellent effects in desensitization treatment. Hence, the present inventors have completed the present invention.

Specifically, the present invention is as described below.

[1] The following recombinant mite allergen (a) or (b):
(a) a recombinant mite allergen comprising the amino acid sequence represented by SEQ ID NO: 2 or 35; or
(b) a recombinant mite allergen comprising an amino acid sequence derived from the amino acid sequence represented by SEQ ID NO. 2 of 35 by deletion, substitution, or addition of one or several amino acids and having mite allergen activity.

[2] A gene encoding the following mite allergen (a) or (b):
(a) a mite allergen comprising the amino acid sequence represented by SEQ ID NO: 2 or 35; or
(b) a mite allergen comprising an amino acid sequence derived from the amino acid sequence represented by SEQ ID NO: 2 or 35 by deletion, substitution, or addition of one or several amino acids and having mite allergen activity.

[3] A gene comprising the following DNA (c) or (d):
(c) a DNA comprising the nucleotide sequence represented by SEQ ID NO: 1 or 34; or
(d) a DNA hybridizing under stringent conditions to a DNA comprising a sequence complementary to that of the DNA comprising the nucleotide sequence of SEQ ID NO: 1 or 34 and encoding a protein having mite allergen activity.

[4] A fragment peptide of the mite allergen according to [1].

[5] The fragment peptide according to [4], which comprises an amino acid sequence that contains at least one of the amino acid sequences represented by SEQ ID NO: 3 to SEQ ID NO: 19.

[6] A fragment gene of a mite allergen, which encodes the fragment peptide according to [4] or [5].

[7] A recombinant vector, which contains the gene according to [2] or [3] or the fragment gene according to [6].

[8] A fusion protein, which is composed of the mite allergen according to [1] and another protein.

[9] A bacterial, yeast, insect, or animal cell, which is transformed using the expression vector according to [7].

[10] A method for producing a recombinant mite allergen, which comprises culturing the bacterial, yeast, insect, or animal cell according to [9] under conditions in which the gene can be expressed, causing the cell to produce a recombinant mite allergen, and then harvesting the recombinant mite allergen.

[11] A method for producing a recombinant mite allergen, which comprises culturing the bacterial, yeast, insect, or animal cell according to [9] under conditions in which the gene can be expressed, causing the cell to produce a fusion recombinant mite allergen, harvesting the fusion recombinant mite allergen, and then eliminating the other protein fused to the allergen.

[12] A therapeutic agent for mite allergic diseases, which contains as an active ingredient the recombinant mite allergen according to [1], the fragment peptide according to [4], or the fusion protein according to [8].

[13] A diagnostic agent for mite allergic diseases, which contains as an active ingredient the recombinant mite allergen according to [1], the fragment peptide according to [4], or the fusion protein according to [8].

[14] An antibody against the mite allergen according to [1].

[15] The antibody against the mite allergen according to [14], which is a monoclonal antibody.

[16] A hybridoma, which produces the monoclonal antibody according to [15].

[17] An immunoassay method for a mite allergen in house dust, which uses the antibody according to any one of [14] to [16].

[18] The immunoassay method for a mite allergen in house dust according to [17], which is the ELISA method.

This specification includes part or all of the contents as disclosed in the description and/or drawings of Japanese Patent Application No. 2004-116089, which is a priority document of the present application.

BRIEF DESCRIPTION OF THE DRAWINGS

FIG. 7-1 shows the partial nucleotide sequence (SEQ ID NO: 1) and amino acid sequence (SEQ ID NO: 2) of a Zen1 gene.

FIG. 7-2 shows the partial nucleotide sequence and amino acid sequence of the Zen1 gene (continuation of FIG. 7-1).

FIG. 8-1 shows the full-length cDNA nucleotide sequence (SEQ ID NO: 34) and amino acid sequence (SEQ ID NO: 35) of the Zen1 gene.

FIG. 8-2 shows the full-length cDNA nucleotide sequence and amino acid sequence of the Zen1 gene (continuation of FIG. 8-1).

FIG. 8-3 shows the full-length cDNA nucleotide sequence and amino acid sequence of the Zen1 gene (continuation of FIG. 8-2).

FIG. 8-4 shows the full-length cDNA nucleotide sequence and amino acid sequence of the Zen1 gene (continuation of FIG. 8-3).

BEST MODE OF CARRYING OUT THE INVENTION

Figure 1:
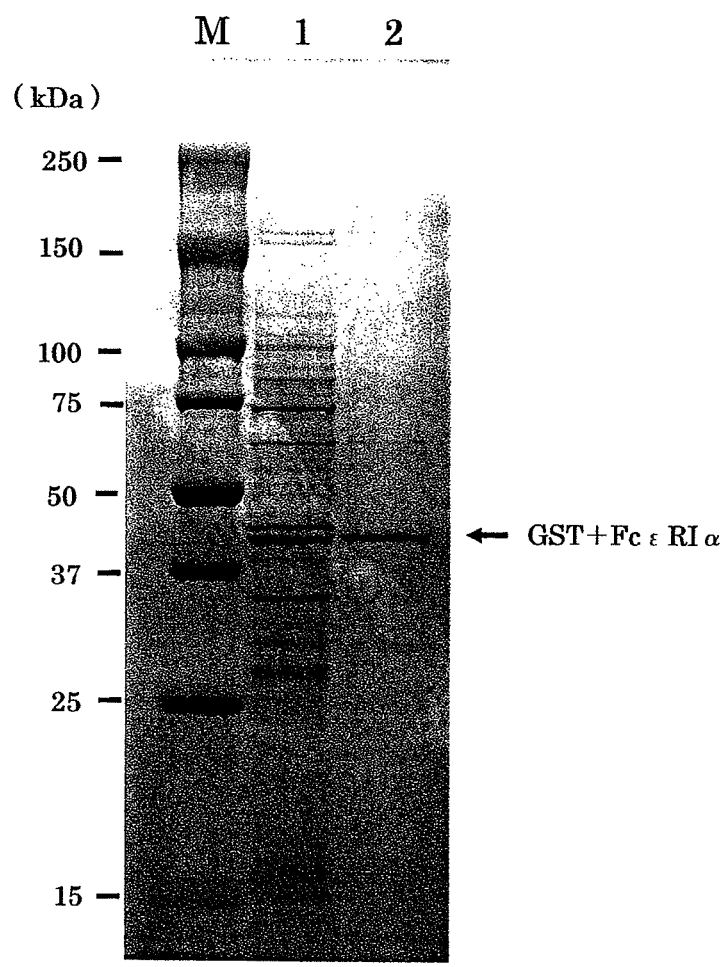
FIG. 1 is a photograph showing the result of electrophoresis of a recombinant dog FcεRIα chain.

The present invention will be described in detail as follows.
(1) Isolation of a Mite Allergen Zen1 Protein and Determination of Partial Sequences Thereof A mite allergy is specified using mite-allergen-specific IgE obtained from an animal clinically diagnosed as having a mite allergy. Specifically, a mite allergen is identified by Western blotting using serum that contains mite-allergen-specific IgE, a mite extract, and an IgE receptor that recognizes allergen-specific IgE, for example. An allergen can be identified by a known method.

The thus identified novel mite allergen of the present invention, which is a Zen1 protein, has a molecular weight between 150 kDa and 200 kDa.

The identified mite allergen can be isolated by performing electrophoresis and then extracting the mite allergen from a mite allergen spot. At such time, it is desired to perform 2-D (two-dimensional) electrophoresis for complete separation from other proteins.

Partial sequences can be determined by a known method using the thus extracted mite allergen. Examples of known methods for determining partial sequences include de novo sequencing based on MS/MS and peptide mapping.
(2) Preparation of cDNA Clone by RT-PCR A DNA encoding the mite allergen of the present invention can be obtained by extracting mRNA from a mite, synthesizing a mite allergen cDNA using the mRNA as a template, constructing a cDNA library, and then screening for the target.

A supply source of such mRNA is a mite body, and the mite is preferably *Dermatophagoides farinae, Dermatophagoides pteronyssinus*, or the like, which are house dust mites. However, the examples are not limited thereto. Such mRNA can be prepared by generally employed techniques. The thus obtained mRNA is used as a template, primers are designed based on the sequence information obtained in (1) above, and then a cDNA fragment encoding a mite allergen is synthesized. The thus obtained fragment is subcloned to an appropriate vector such as pGEM (produced by Promega). The nucleotide sequence is then determined by a standard method such as a cycle sequencing method.

Partial amino acid sequences of the mite allergen of the present invention are shown in SEQ ID NOS: 3 to 19. Of these, the sequences shown in SEQ ID NOS: 3 to 7 were determined by de novo sequencing. An N-terminal amino acid sequence is shown in SEQ ID NO: 19. The sequences shown in SEQ ID NOS: 8 to 18 were determined by peptide mapping.

The present invention includes a mite allergen that comprises an amino acid sequence comprising at least one of the amino acid sequences shown in SEQ ID NOS: 3 to 19 that represent fragments of the Zen1 protein, which is a mite allergen.

A partial nucleotide sequence of the DNA of the Zen1 gene encoding the Zen1 protein, which is the mite allergen of the present invention, is shown in SEQ ID NO: 1, and the full-length nucleotide sequence thereof is shown in SEQ ID NO: 34. A partial amino acid sequence of the Zen1 protein, which is the mite allergen of the present invention, is shown in SEQ ID NO: 2, and the full-length amino acid sequence thereof is shown in SEQ ID NO: 35.

As long as a protein comprising such amino acid sequence has mite allergen activity, mutations such as deletion, substitution, or addition of at least one, and preferably one or several, amino acid(s) may take place in the amino acid sequence.

For example, at leak one, and preferably one or several (e.g., 1 to 10 and further preferably 1 to 5), amino acid(s) of the amino acid sequence represented by SEQ ID NO: 2 or SEQ ID NO: 35 may be deleted. At least one, and preferably one or several (e.g., 1 to 10 and further preferably 1 to 5), amino acid(s) may be added to the amino acid sequence represented by SEQ ID NO: 2. Alternatively, at least one, and preferably one or several (e.g., 1 to 10 and further preferably 1 to 5), amino acid(s) of the amino acid sequence represented by SEQ ID NO: 2 may be substituted with (an)other amino acid(s).

Examples of such amino acid sequence derived from the amino acid sequence of SEQ ID NO: 2 or SEQ ID NO: 35 by deletion, substitution, or addition of one or several amino acids include amino acid sequences having at least 85% or more, preferably 90% or more, further preferably 95% or more, and particularly preferably 97% or more homology with the amino acid sequence of SEQ ID NO: 2 or SEQ ID NO: 35 as calculated using BLAST (Basic Local Alignment Search Tool at the National Center for Biological Information) using default parameters for initial setting, for example.

A protein having such amino acid sequence derived from the amino acid sequence of SEQ ID NO: 2 or SEQ ID NO: 35 by deletion, substitution, or addition of one or several amino acids is substantially the same as the protein having the amino acid sequence of SEQ ID NO: 2 or SEQ ID NO: 35.

Furthermore, examples of the gene of the present invention also include a DNA that is capable of hybridizing under the following conditions to a DNA comprising a sequence complementary to that of a gene having the DNA sequence shown in the above SEQ ID NO: 1 or SEQ ID NO: 34 and that encodes a protein having mite allergen activity. Specifically, such conditions enable identification by hybridization in the presence of 0.7 M to 1.0 M NaCl at 68° C. using a filter on which a DNA is immobilized and washing with the use of a 0.1 to 2×SSC solution (1×SSC comprises 150 mM NaCl and 15 mM sodium citrate) at 68° C. Alternatively, the gene of the present invention is a DNA that can form a hybrid when it is transferred to and immobilized on a nitrocellulose membrane by the Southern blotting method and then allowed to react overnight at 42° C. in a hybridization buffer (50% formamide, 4×SSC, 50 mM HEPES (pH 7.0), 10×Denhardt's solution, and 100 µg/ml salmon sperm DNA).

Furthermore, the present invention also includes an RNA corresponding to the above DNA or an RNA capable of hybridizing under stringent conditions to the RNA and encoding a protein having mite allergen activity.

The recombinant vector of the present invention can be obtained by ligating (inserting) the gene of the present invention into an appropriate vector. Vectors for use in insertion of the gene of the present invention are not particularly limited as long as they are replicable in hosts such as bacteria, yeast, or animal cells. Examples of such vectors include a plasmid DNA and a phage DNA. A vector DNA that is used for construction of an expression vector is widely disseminated and easily obtained. Examples of such vector DNA include pUC19 and pTV118 N (produced by Takara Shuzo), pUEX2 (produced by Amersham), pGEX-4T and pKK233-2 (produced by Pharmacia), and pMAM-neo (produced by Clontech).

A method for constructing such expression vector of the present invention is not particularly limited and can be performed according to a standard method. For example, a mite allergen cDNA fragment digested with EcoR I can be inserted into the EcoR I site in the plasmid pUC19 multicloning site. Furthermore, the fragment can be ligated to the EcoR I site of a plasmid vector pGEX-4T, so that an expression vector can be obtained.

Bacteria, yeast, or animal cells transformed with such expression vector of the present invention are not particularly limited, as long as they can express the gene of the present invention. Examples of such bacteria include *Escherichia coli* and *Bacillus subtilis*. Examples of such yeast include *Saccharomyces cerevisae* and the like. Examples of such animal cells include Chinese hamster ovary (CHO) cells, Sf21 and Sf9 cells which are *Mamestra brassicae* ovarian cells, monkey COS cells, and mouse fibroblasts.

Examples of the recombinant mite allergen of the present invention include, in addition to mite allergens that are directly expressed, those expressed as fusion proteins with other proteins. Hereinafter, such fusion proteins are referred to as fusion recombinant mite allergens. Examples of other proteins that form such fusion proteins include, but are not particularly limited to, β-galactosidase, glutathione S-transferase, protein A, and a maltose-binding protein.

The recombinant mite allergen of the present invention may also be a peptide fragment consisting of only a region essential for allergen activity or a peptide fragment comprising a region essential for allergen activity. Moreover, in addition to a product obtained by expression of a mite allergen protein alone, such recombinant mite allergen may be obtained from a product expressed as a fusion protein by eliminating the other protein(s).

Specifically, the recombinant mite allergen of the present invention is obtained by expression of a gene derived from a mite body and is a protein having mite allergen activity. Here, "having mite allergen activity" means to be capable of inducing an allergy reaction in a mammal.

The mite allergen of the present invention can be produced by the following methods. After completion of culture of the above transformant strain, microbial bodies are harvested, suspended in a buffer containing various protease inhibitors, and then disrupted by ultrasonication. A membrane-localized protein in cell debris is extracted using a buffer containing a protease inhibitor such as phenylmethanesulfonyl fluoride, monoiodoacetic acid, pepstatin A, or ethylenediaminetetraacetic acid and a surfactant such as sodium lauryl sulfate (SDS), triton X-100, or Nonidet P40. A fusion protein composed of the mite allergen and glutathione S-transferase obtained from the extract or the culture concentrate is purified by affinity chromatography using immobilized glutathione, affinity chromatography using immobilized anti-mite body antibody, or the like. In addition, a carrier on which glutathione is immobilized is a carrier produced by Pharmacia. Furthermore, a carrier on which an anti-mite body antibody is immobilized is a carrier prepared by covalently binding a rabbit anti-mite body antibody to an activated Tresyl carrier (e.g., Tresyl GM gel (produced by Kurita Water Industries), Tresyl Toyopearl (produced by Tosoh), and Tresyl sepharose (produced by Pharmacia)). Furthermore, a fusion protein composed of a mite allergen and a His tag (e.g., 6×His) can be obtained, followed by purification using affinity beads to which a metal is immobilized, or the like.

The purified fusion recombinant mite allergen is digested with protease and then fractionated by a single or a combination of known purification method(s) including gel filtration chromatography, ultrafiltration, ion exchange chromatography, affinity chromatography, hydrophobic chromatography, chromatofocusing, an isoelectric focusing method, and a gel electrophoresis method while monitoring takes place with ELISA and a leukocyte histamine release test for mite allergic disease patients (Allergy 37, 725 (1988)).

The present invention also encompasses a therapeutic agent for mite allergic diseases containing a mite allergen as an active ingredient. Such therapeutic agent is used as a therapeutic agent for various types of mite allergic diseases. Here, "mite allergic diseases" means all allergic diseases that are caused by mite-specific antigens, such as atopic bronchial asthma, allergic rhinitis, allergic conjunctivitis, and atopic dermatitis.

The therapeutic agent for mite allergic diseases of the present invention can be prepared by drying a recombinant mite allergen or a fragment peptide thereof purified by the above method, harvesting such allergen or fragment peptide in a powdery form, and then preparing a therapeutic desensitizing agent for mite allergic diseases, for example. However, the method is not particularly limited thereto. When the therapeutic agent for mite allergic diseases of the present invention is used as a therapeutic desensitizing agent, the agent can be directly used or, if necessary, used as a combination drug supplemented by a standard method with a generally used adjuvant and various additive agents such as a stabilizing agent, an excipient, a solubilizing agent, an emulsifying agent, a buffer agent, a soothing agent, a preservative, and a coloring agent. For example, a purified recombinant mite allergen in a powdery form is dissolved in physiological saline supplemented with phenol and then used as a stock solution for an antigen for desensitization treatment.

The therapeutic agent for mite allergic diseases of the present invention can be administered via general routes of administration such as percutaneous, oral, intracutaneous, subcutaneous, intramuscular, and intraperitoneal administration methods. Furthermore, the therapeutic agent of the present invention can also be used in a percutaneous or transmucosal drug such as a troche, a sublingual tablet, an eye drop, an intranasal spray agent, a poultice, a cream, and a lotion. Furthermore, the dose and the number of instances of administration of the therapeutic agent for mite allergic diseases of the present invention are appropriately selected depending on the route of administration, symptoms, and the like, so that the dose is within a range of approximately 20 μg or less per instance of administration for an adult. Administration is performed once or several times a week.

Furthermore, the therapeutic agent for mite allergic diseases of the present invention is useful not only as a therapeutic agent against mite allergic diseases, but also as a prophylactic agent against the same. Moreover, the therapeutic agent for mite allergic diseases of the present invention can be safely used for human bodies without the exertion of anaphylaxis-inducing action.

The diagnostic agent for mite allergic diseases of the present invention is used as a reagent for diagnosing intracutaneous reactions against mite allergic diseases or a titration reagent for diagnosing mite allergies. When the diagnostic agent is used as a reagent for diagnosing intracutaneous reactions, the reagent is obtained by preparing a recombinant mite allergen or a fragment peptide thereof purified by the above method according to a standard method. For example, a recombinant mite allergen is dried and powdered, the powder is dissolved and diluted in physiological saline containing phenol, and then it is used. A method using the diagnostic agent as a reagent for diagnosing intracutaneous reactions is employed according to a standard method.

Furthermore, when the diagnostic agent is used as a titration reagent for diagnosing mite allergies, the reagent is prepared similarly by a standard method. For example, a recombinant mite allergen or a fragment peptide thereof is appropriately dissolved and diluted in a Hank's buffer, so that the resultant is used as a reagent for histamine release titration. This method is generally performed by the following procedures. Specifically, blood of a mite allergic disease patient or a blood cell fraction obtained by centrifugation from the blood of the patient is suspended in a buffer. A fixed amount of the blood cell suspension is subjected to titration using a recombinant mite allergen as a titration reagent. The amount of histamine that is released from basophils by allergen stimulation is measured using HPLC [Allergy 37, 725 (1988)].

In the histamine release titration, the amount of histamine to be released is determined based on 50% (inflexion point of the titration curve) of the maximum release amount. Specifically this titration is characterized in that: (1) a patient's allergen sensitivity is directly measured based on a titer of a blood cell suspension; and (2) after pre-reaction of blood plasma with a recombinant mite allergen, the value (blood titration curve value) obtained by titrating the blood cell suspension with the reaction solution is usually higher than the value (blood cell suspension titration curve value) obtained by titrating the blood cell suspension with the recombinant mite allergen. This is due to the presence of an IgG antibody (blocking antibody) capable of allergen neutralization in blood plasma. Therefore, the blocking antibody titer can be obtained from the degree to which the blood titration curve has shifted from the blood cell suspension titration curve. The allergen sensitivity and this blocking antibody titer enable accurate mite allergy diagnosis feasible. This histamine release titration test is also useful for monitoring the effect of desensitization treatment.

The present invention also encompasses an antibody against the mite allergen of the present invention or a fragment peptide thereof. Such antibody can be obtained as a polyclonal antibody or a monoclonal antibody by a known method. Such antibody can be used for measuring the presence, the absence, or the like of a mite allergen in house dust, for example. Such measurement can be performed by a known immunological method such as ELISA. Upon such measurement, a protein is extracted from house dust and then measured.

In addition, the recombinant mite allergen protein of the present invention is expressed. By conducting a test such as a specific IgE reaction test or an intracutaneous reaction test with a mite allergy patient dog using the thus expressed recombinant protein, the allergen protein functions of the mite allergen protein of the present invention can be confirmed.

The present invention will be further described in the following examples. The examples are not intended to limit the scope of the invention.

In addition, reagents used in each example were commercial reagents purchased from Nacalai Tesque, Wako Pure Chemical Industries, Sigma, Difco, or the like, unless otherwise specified. Furthermore, reagents for genetic engineering, such as restriction enzymes were purchased from Takara Shuzo, Toyobo, Invitrogen, or the like and then used according to the manufacturers' instructions.

Example 1

Establishment of an IgE Detection System

Figure 2:
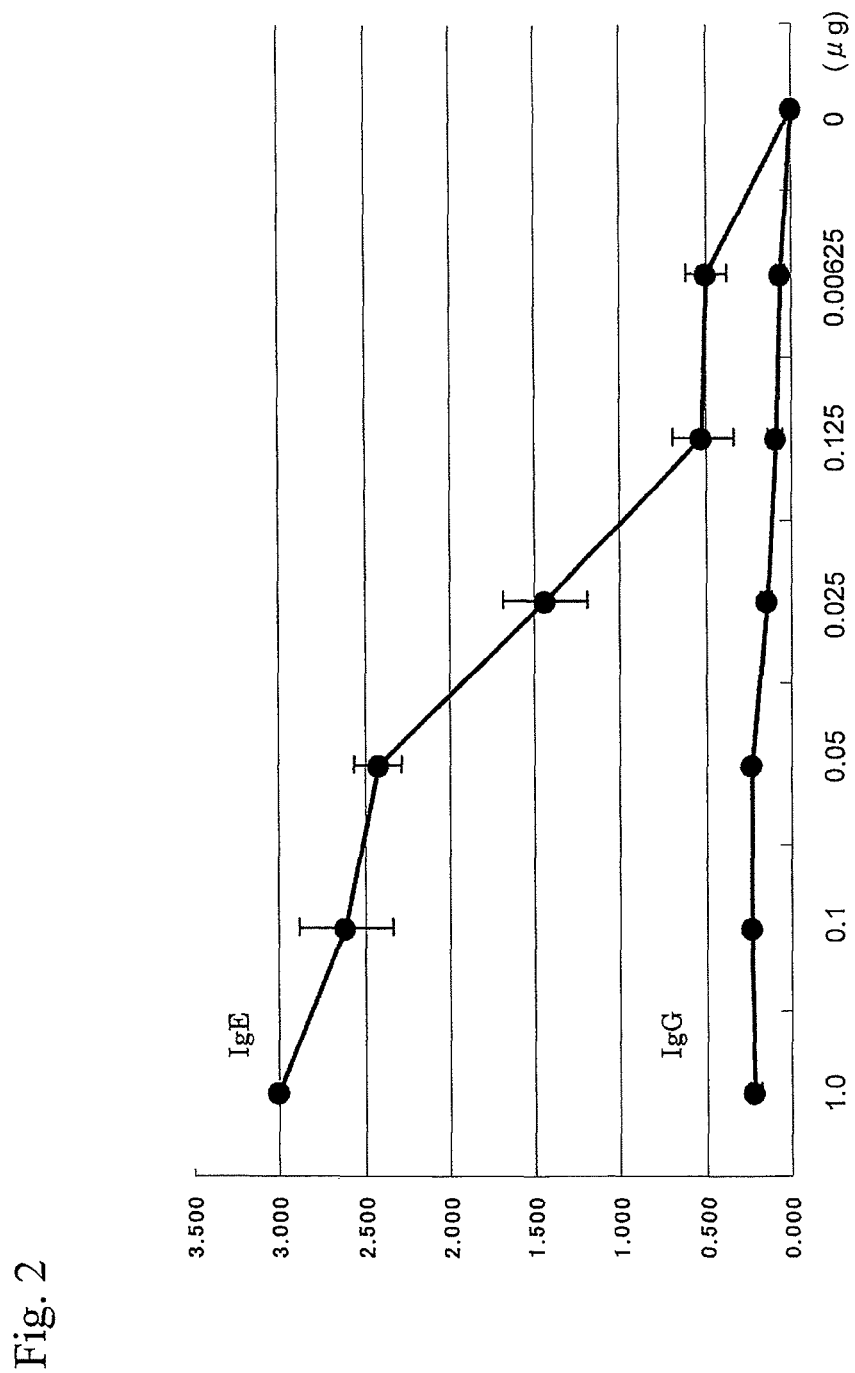
FIG. 2 is a graph showing the binding of a recombinant dog FcεRIα chain with IgE.
Figure 3:
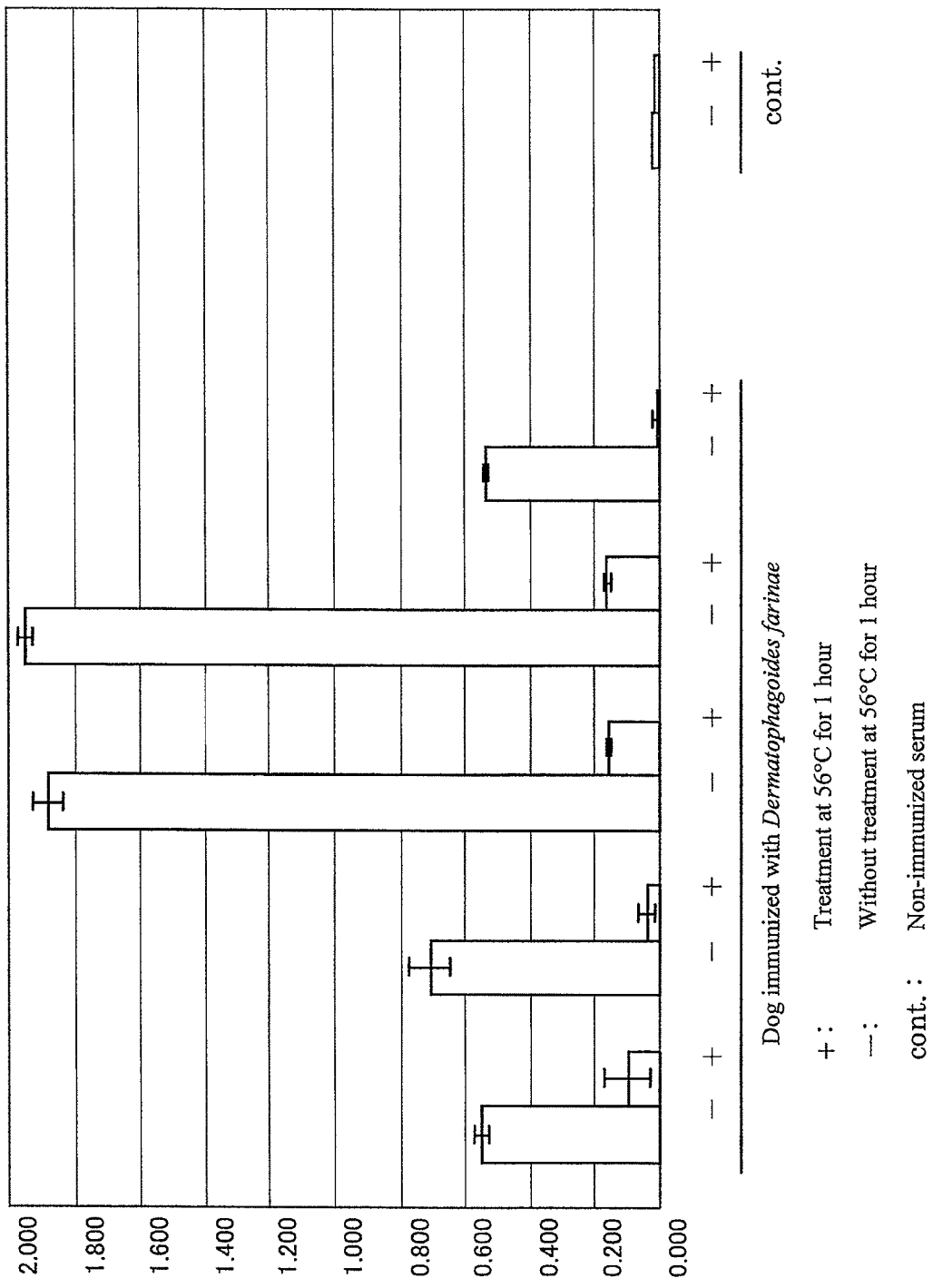
FIG. 3 shows the result of detecting *Dermatophagoides farinae*-specific IgE.

The extracellular region of a dog high-affinity IgE receptor α chain (FcεRIα) cDNA, excluding its signal peptide site and having had restriction enzyme EcoR I and Xho I sites added thereto, was amplified by PCR. The resultant was ligated to the EcoR I and Xho I sites of *Escherichia coli* expression plasmid vector pGEX4T-1 (produced by Amersham Biosciences) using T4-DNA ligase. An *E. coli* TOP10 strain (produced by Invitrogen) was transformed with the thus obtained recombinant plasmid. The transformed strain was cultured at 37° C. overnight in an LB medium containing ampicillin (100 µg/mL). Subsequently, a small amount of the strain was subcultured on a new LB medium until OD at 600 nm reached 1.0. Next, IPTG (isopropyl-1-thio-β-D-galactoside) was added to a final concentration of 1 mM. 3 hours later, cells were harvested and then washed once with PBS (pH 7.4). Cells harvested again were lysed by ultrasonication in PBS (pH 7.4), insoluble fractions were removed by centrifugation, and then soluble fractions containing dog FcεRIα fused to glutathione S-transferase (GST) were collected. Subsequently, dog FcεRIα fused to GST was obtained from the soluble fractions using a glutathione sepharose 4B column (produced by Amersham Biosciences). 1.0 mg of the fusion protein (GST-FcεRIα) was obtained from 10 liters of the culture solution. It was confirmed that the obtained purified GST-FcεRIα showed a single band of 45 kDa as a result of SDS-PAGE (FIG. 1). Recombinant dog IgE (produced by BETHYL) and purified dog IgG were immobilized on an immunoplate (produced by Nalge Nunc International) with 2-fold serial dilution from 1.0 µg, 0.1 µg, 0.05 µg, 0.025 µg, 0.0125 µg, and then 0.00625 µg, so as to confirm the reactivity of the purified GST-FcεRIα. It was confirmed that the purified GST-FcεRIα reacted with IgE but did not react with IgG (FIG. 2). 4.0 µg of an antigen extracted from *Dermatophagoides farinae* (produced by GREER) was immobilized on an immunoplate (produced by Nalge Nunc International). *Dermatophagoides-farinae*-positive dog serum (dog serum that tested positive for *Dermatophagoides farinae* as confirmed by an intracutaneous reaction using a *Dermatophagoides farinae* antigen solution (produced by GREER) diluted 50-fold using physiological saline) was caused to react with the antigen. Biotin-labeled GST-FcεRIα was then added. Furthermore, based on a color development reaction resulting from the addition of peroxidase conjugate streptavidin (produced by Jackson Immuno Research) and a substrate, it was confirmed that the GST-FcεRIα chain recognized mite-allergen-specific IgE (FIG. 2). Furthermore, 4.0 µg of an antigen extracted from *Dermatophagoides farinae* (produced by GREER) was immobilized on an immunoplate (produced by Nalge Nunc International). Dog serum obtained by immunization with the antigen extracted from *Dermatophagoides farinae* was caused to react with the antigen. It was confirmed that the GST-FcεRIα reacted with neither *Dermatophagoides-farinae*-positive dog serum subjected to heat treatment at 56° C. for 1 hour nor dog purified IgG, but reacted with the recombinant dog IgE (produced by BETHYL). It was thought that the GST-FcεRIα recognized allergen-specific IgE (FIG. 3). In FIG. 3, "−" denotes serum not treated at 56° C. for 1 hour, "+" denotes serum treated at 56° C. for 1 hour, and "cont." denotes non-immunized serum.

Example 2

Analysis of a Major Mite Allergen by Western Blotting

Figure 4:
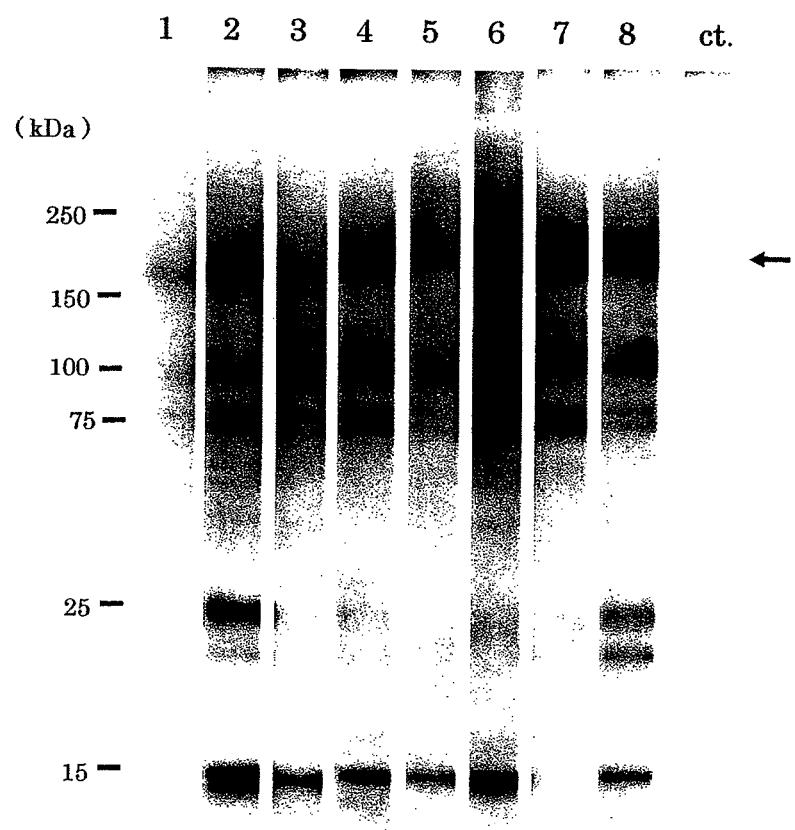
FIG. 4 is a photograph showing the results of Western blot analysis using a recombinant dog FcεRIα chain.

Western blot analysis was conducted using the sera and blood plasma samples of eight dogs. The eight dogs had developed atopic dermatitis and had been diagnosed with mite allergies based on intracutaneous reactions using the solution of an antigen extracted from a *Dermatophagoides farinae* allergen (produced by GREER) and the ELISA method using the recombinant dog FcεRIα chain established in Example 1. β-mercaptoethanol was added to 100.0 μL of the solution of an antigen extracted from *Dermatophagoides farinae* to a final concentration of 50.0 μL/mL. 200 μL of the thus prepared Laemmli sample buffer (produced by BIO-RAD) was added, followed by heat treatment at 100° C. for 5 minutes. The resultant was applied to polyacrylamide gel (PAGEL; produced by ATTO) with a gel concentration between 5% and 20%, and then electrophoresis was performed. After completion of electrophoresis, the resultant was transferred to a PVDF membrane (Hybond-P; produced by Amersham Biosciences). The membrane was allowed to stand at 4° C. overnight in a blocking solution (PBST (prepared by adding Tween20 to PBS to a final concentration of 0.1%) supplemented with 5% skim milk). After the membrane had been washed in PBST for 10 minutes, each dog serum or blood plasma sample was diluted 10-fold in a blocking solution. Each diluted solution sample was added to the membrane, followed by 3 hours of reaction at room temperature. Three instances of washing (10 minutes each) were performed with PBST. Biotin-labeled dog FcεRIα was diluted with a blocking solution and then the diluted solution was added to the membrane, followed by 2 hours of reaction at room temperature. After 3 instances of washing (10 minutes each) with PBST, a streptavidin-HRP conjugate (produced by Amersham Biosciences) diluted 10,000-fold with PBST was added to the membrane, followed by 1 hour of reaction at room temperature. After 5 instances of washing (10 minutes each) with PBST, a reaction solution for an ECL Plus Western blotting detection system (produced by Amersham Biosciences) was added onto the membrane, followed by 5 minutes of reaction at room temperature. Signals were then detected using X-ray film (Hyperfilm ECL; produced by Amersham Biosciences). As a result, a protein showing a strong reaction was detected between a band corresponding to a molecular weight of 150 kDa and a band corresponding to the same of 250 kDa (FIG. 4). In FIG. 4, a band indicated with an arrow corresponds to the protein showing a strong reaction and having a molecular weight between 150 kDa and 250 kDa. In FIG. 4, numerals from 1 to 8 separately denote eight dogs, and "ct." denotes a negative serum.

Example 3

Analysis of a Mite Allergen Protein by 2-D (Two-Dimensional) Electrophoresis

Figure 5:
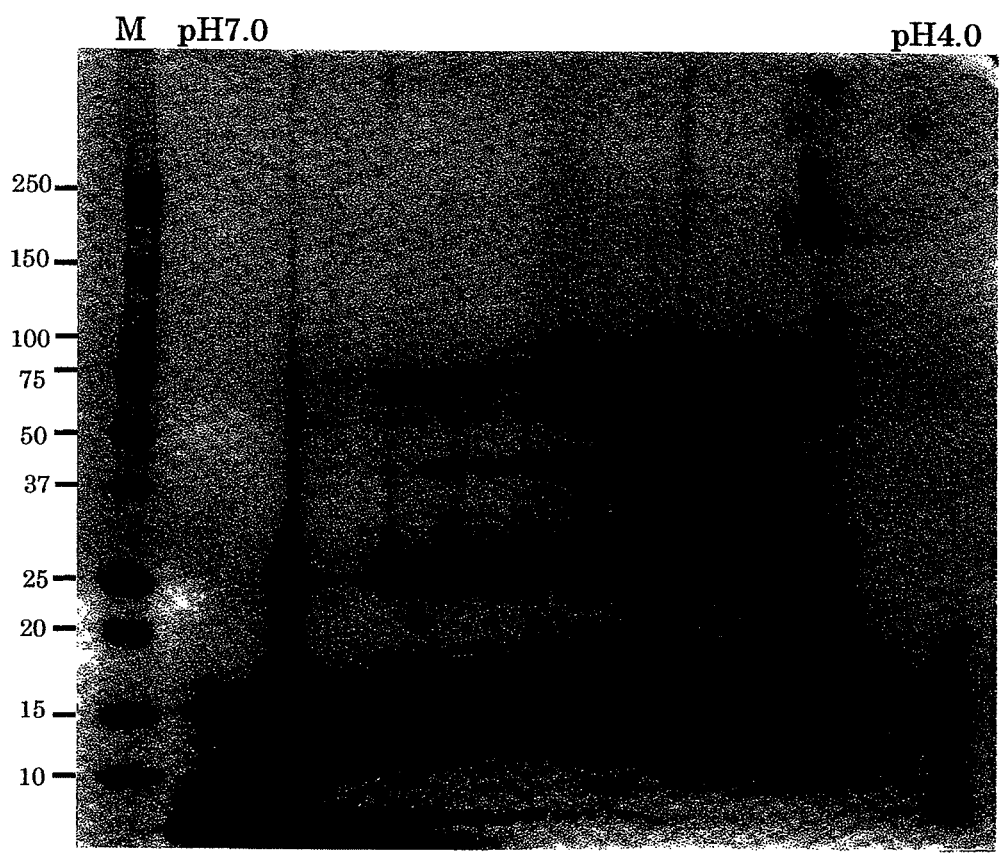
FIG. 5 is a photograph showing a 2-D (two-dimensional) electrophoresis pattern of an antigen extracted from *Dermatophagoides farinae*.

An allergen protein with a molecular weight between 150 kDa and 250 kDa, with which IgE had strongly reacted, was isolated by 2-D (two-dimensional) electrophoresis. 2-D (two-dimensional) electrophoresis was performed using a Protean IEF cell (produced by BIO-RAD) 1.0 mg of an antigen extracted from *Dermatophagoides farinae* (produced by GREER) was dissolved in 1.0 mL of a swelling buffer (2-D starter kit; produced by BIO-RAD). 300 μL of the thus obtained solution was swollen under active conditions (50 V, 20° C., and 12 hours) using 17-cm-long IPG Ready strip gel (pH 4-7, produced by BIO-RAD) and a focusing tray. After swelling, focusing was performed under the following conditions. First, a procedure to remove excessive salts was performed in step 1 (250 V, 20 minutes, and 20° C.). In step 2, voltage was elevated from 250 V to 10,000 V for 6 hours. In step 3, focusing was performed with a voltage of 10,000 V and with voltage hours totaling 60,000 VH. Before 2-D (two-dimensional) electrophoresis, the IPG ready strip gel was gently shaken for 10 minutes using SDS-PAGE equilibrated buffer I (6 M urea, 0.375 M Tris pH 8.8, 2% SDS, 20% glycerol, and 2% (w/v) DTT; produced by BIO-RAD). Subsequently, the gel was further gently shaken for 10 minutes using SDS-PAGE equilibrated buffer II (6 M urea, 0.375 M Tris pH 8.8, 2% SDS, 20% glycerol, and 2.5% (w/v) iodoacetamide; produced by BIO-RAD), thereby performing equilibration. The equilibrated IPG ready strip gel was caused to closely adhere to PII ready gel (8-16%; produced by BIO-RAD) using 1% (v/w) low melt agarose (produced by BIO-RAD). Electrophoresis was performed with a 40-mA constant current (with initial voltage of 135 V and final voltage of 400 V) for approximately 3 hours. After electrophoresis, the gel was stained using Bio-Safe (produced by BIO-RAD), so that pattern analysis could be conducted for the protein spot (FIG. 5).

Example 4

Identification of an Allergen Spot by Western Blot Analysis

Figure 6:
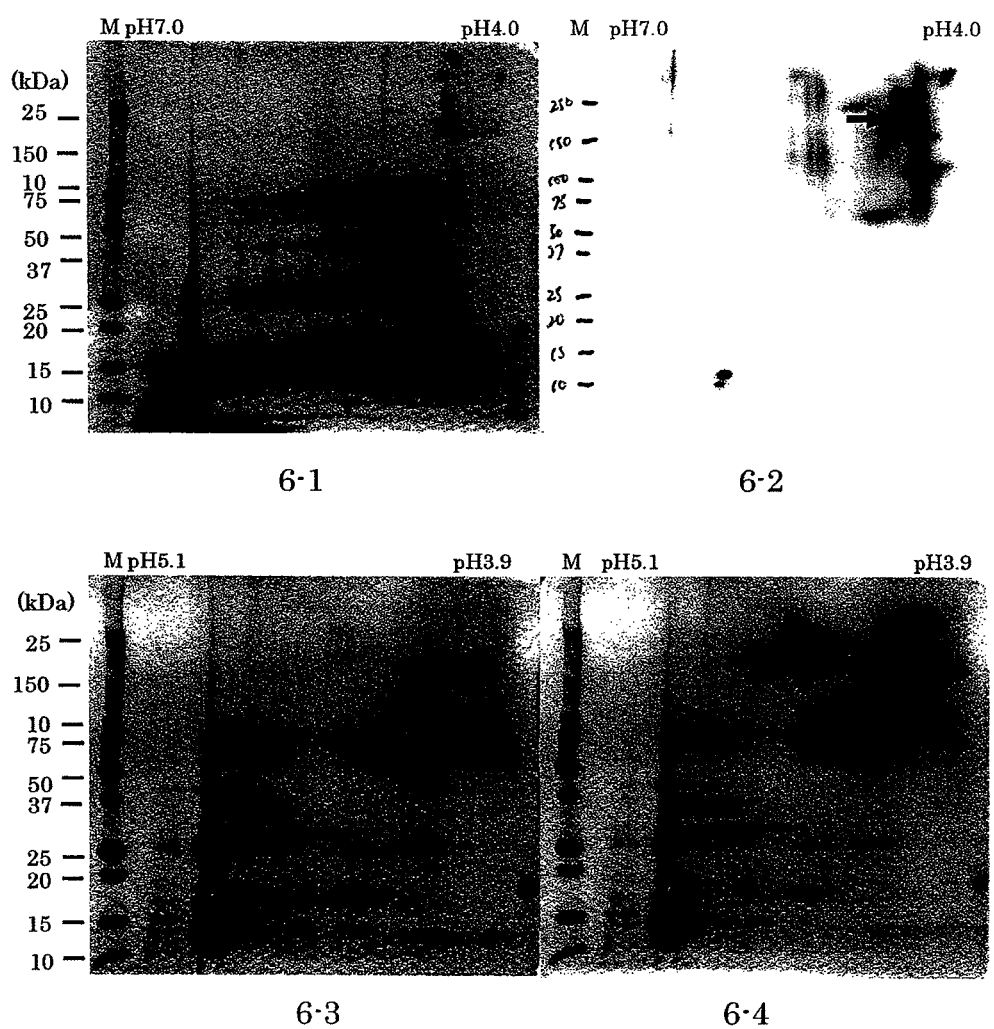
FIG. 6 shows photographs showing the results of 2-D (two-dimensional) electrophoresis and Western blot analysis of a *Dermatophagoides farinae* allergen protein.

After 2-D (two-dimensional) electrophoresis, the protein spot was transferred to a PVDF membrane (Hybond-P; produced by Amersham Biosciences). The membrane was allowed to stand at 4° C. overnight in a blocking solution (PBST (prepared by adding Tween20 to PBS to a final concentration of 0.1%) supplemented with 5% skim milk). After the membrane had been washed with PBST for 10 minutes, a dog serum or blood plasma sample was diluted 10-fold using a blocking solution. The thus diluted solution was added to the membrane, followed by 3 hours of reaction at room temperature. After 3 instances of washing (10 minutes each) with PBST, biotin-labeled dog FcεRIα was diluted with a blocking solution. The diluted biotin-labeled dog FcεRIα was added to the membrane, followed by 2 hours of reaction at room temperature. After 3 instances of washing (10 minutes each) with PBST, a streptavidin-HRP conjugate (produced by Amersham Biosciences) diluted 10,000 fold with PBST was added to the membrane. One hour of reaction was performed at room temperature. After 5 instances of washing (10 minutes each) with PBST, a reaction solution for an ECL plus Western blotting detection system (produced by Amersham Biosciences) was added onto the membrane, followed by 5 minutes of reaction at room temperature. Signals were detected using X-ray film (Hyperfilm ECL; produced by Amersham Biosciences). As a result, a spot showing a strong reaction was detected between a band corresponding to a molecular weight of 150 kDa and a band corresponding to the same of 250 kDa and at a pH of about 4.5. Thus, the spot corresponding to the allergen protein (Zen1) of the present invention was obtained (FIG. 6). In FIG. 6: upper left FIG. 6-1 shows the 2-D (two-dimensional) electrophoresis pattern (pH 4 to 7) of *Dermatophagoides farinae*; upper right FIG. 6-2 shows the result of Western blot analysis (pH 4 to 7) using the *Dermatophagoides-farinae*-positive serum of a dog patient developing atopic dermatitis; lower left FIG. 6-3 shows the 2-D (two-dimensional) electrophoresis pattern (pH 3.9 to 5.1) of *Dermatophagoides farinae*; and lower right FIG. 6-4 shows the reaction spot (where the spot appears as a black circular spot on the upper portion in the figure and is indicated with an arrow) obtained by Western blot analysis (pH 3.9 to 5.1) using the *Dermatophagoides farinae*-positive serum of a dog patient developing atopic dermatitis, as compared with the 2-D (two-dimensional) electrophoresis pattern. A strong reaction was observed for the spot indicated with the arrow.

Example 5

Proteome Analysis of the Zen1 Protein

The Zen1 protein spot isolated by 2-D (two-dimensional) electrophoresis was excised from the gel and then MS/MS analysis was conducted. A great deal of MS/MS data could be obtained, but no hits were confirmed. Five peptides thought to be novel proteins were subjected to the de novo sequencing method, so that amino acid sequences (SEQ ID NOS: 3 to 7) were determined (Table 1). BLAST search was performed for these amino acid sequences, but no clear hits were obtained.

TABLE 1

| | |
|---|---|
| Partial sequence 415 | MKSLLNEANELLK |
| Partial sequence 445 | SAQDVLEK |
| Partial sequence 847 | FMQSLLNEADELLR |
| Partial sequence 448 | LPDSDLKDELAK |
| Partial sequence 491 | LPDSDLKNELAEK |

Partial amino acid sequences of Zen1 as determined by the de novo sequencing method.

Example 6

Peptide Mapping Analysis of the Zen1 Protein

The Zen1 protein spot isolated by 2-D (two-dimensional) electrophoresis was excised from the gel. A peptide map was prepared and then amino acid sequencing was performed for 8 peaks. As a result, sequences (SEQ ID NOS: 8 to 18) of 11 amino acid fragments were determined (Table 2). BLAST search was performed, but no clear hits were obtained.

TABLE 2

| | |
|---|---|
| Partial sequence 21 | MYNFHLEAY |
| Partial sequence 28 | IAHFLELE |
| Partial sequence 32 | IAHFELE |
| Partial sequence 23-1 | KFQSLLNEAN |
| Partial sequence 23-2 | IAHLESE(T) |
| Partial sequence 24 | KFQSLLN(E)A |
| Partial sequence 22 | DAQLEXE |
| Partial sequence 9-1 | SAQDVSL |
| Partial sequence 9-2 | RNEMNE |
| Partial sequence 20-1 | MFQSLLNKADFD |
| Partial sequence 20-2 | DLARDVXL |

Amino acid sequences corresponding to peaks obtained by peptide mapping of Zen1

Example 7

Analysis of the N-Terminal Amino Acid Sequence of the Zen1 Protein

The Zen1 protein spot isolated by the 2-D (two-dimensional) electrophoresis was excised from the gel. The N-terminal amino acid sequence (SEQ ID NO: 19) of the Zen1 protein was determined by a standard method using an HP G1005A protein sequencing system (Table 3). BLAST search was performed for the sequence, but no clear hits were obtained.

TABLE 3

| | |
|---|---|
| N-terminal sequence | DNRDDVLKQTEE |

Zen1 N-terminal amino acid sequence

Example 8

Extraction of Mite Total RNA and Separation of Mite Poly(A) mRNA

Untreated mite bodies obtained by culturing and growing *Dermatophagoides farinae* according to a standard method were placed in approximately 2.0 L of a saturated saline solution. The solution was agitated well and then allowed to stand for 30 minutes. Mite bodies in the supernatant were skimmed using a strainer, washed using physiological saline, and then dried 1.0 g of mite bodies was subjected to total RNA extraction and mite poly(A) mRNA separation using a Past-Track 2.0 kit (produced by Invitrogen) according to the manual of the kit.

Example 9

Synthesis of Mite cDNA

Reverse transcription reaction was performed using 100 ng of the mite poly(A) mRNA separated in Example 8 as a template and a cDNA synthesis kit (ReverTraAce-α-; produced by Toyobo) according to the manual of the kit.

Example 10

Amplification of the Zen1 Gene by PCR

Based on the N-terminal amino acid sequence of the Zen1 protein, primers N-1 (5'-GAYGAYGTNTTRAARCARAC-NGARGAR-3' (SEQ ID NO: 20): Y=C or T, N=A or C or G or T, and R=A or G) and N-2 (5'-GAY GAY GTN CTN AAR CAR ACN GAR GAR-3' (SEQ ID NO: 21): Y=C or T, N=A or C or G or T, and R=A or G) were designed as sense primers. Furthermore, 12 primers (SEQ ID NOS: 22 to 33) were designed based on the amino acid sequences obtained by the de novo sequencing method (Table 4) as reverse primers. With the use of 1.0 μg of the mite cDNA synthesized in Example 9 as a template, Ex taq polymerase (produced by TaKaRa Bio), and each sample prepared according to the manual, thermal denaturation treatment was performed at 94° C. for 2 minutes and 35 cycles of reaction, each of which consisted of 94° C. for 1 minute, 65° C. for 2 minutes, and 72° C. for 3 minutes were performed. After further reaction was performed at 72° C. for 9 minutes, the sample was stored at 4° C. A DNA fragment of approximately 1,000 bp was obtained when PCR was performed using a reverse primer 415-4 (5'-RTTNAGNAGRTCYTTNGCRTCYTT-3' (SEQ ID NO: 25): N=A or C or G or T, R=A or G, and Y=C or T). A DNA fragment of approximately 880 bp was obtained when PCR was performed using 491-2 (5'-RTT RTC NGC NAG RTC YTT RTT-3 (SEQ ID NO: 29): N=A or C or G or T, R=A or G, and Y=C or T).

TABLE 4

| | |
|---|---|
| N-1 | 5'- GAY GAY GTN TTR AAR CAR ACN GAR GAR -3' |
| N-2 | 5'- GAY GAY GTN CTN AAR CAR ACN GAR GAR -3' |
| 415-1 | 5'- RTT RAA RAA RTC YTT NGC RTC YTT RAA -3' |
| 415-2 | 5'- RTT NAG RAA RTC YTT NGC RTC YTT -3' |

TABLE 4-continued

```
415-35'- RTT RAA NAG RTC YTT NGC RTC YTT -3'

415-45'- RTT NAG NAG RTC YTT NGC RTC YTT -3'

445-15'- RTT RTC RAA NAC YTC RTG NGC -3'

445-25'- RTT RTC NAG NAC YTC RTG NGC -3'

491-15'- RTT RTC NGC RAA RTC YTT RTT -3'

491-25'- RTT RTC NGC NAG RTC YTT RTT -3'

448-15'- RTT NGC RAA RTC YTC RTT RAA YTC -3'

448-25'- RTT NGC NAG RTC YTC RTT RAA YTC -3'

448-35'- RTT NGC RAA RTC YTC RTT NAG YTC -3'

448-45'- RTT NGC NAG RTC YTC RTT NAG YTC -3'
```

Mixture primer sequences synthesized for amplification of the Zen1 gene.
A fragment of approximately 1000 bp was obtained when PCR was performed using N-1 and 415-4.
A fragment of approximately 880 bp was obtained when PCR was performed using N-1 and 491-2.
N = A or C or G or T, R = A or G, Y = C or T Example 11

Cloning of the Zen1 Gene

The DNA fragment amplified using the primers N-1 and 415-4 in Example 10 was collected from the agarose gel (SUPREC-01 produced by TaKaRa). The DNA fragment was ligated to the cloning site of pGEM-T Easy Vector (produced by Promega) using T4 DNA ligase, thereby transforming host *Escherichia coli* TOP10 (produced by Invitrogen). Specifically, *Escherichia coli* competent cells and a plasmid were mixed and then the mixture was subjected to temperature treatment on ice for 30 minutes, at 42° C. for 30 seconds, and on ice for 2 minutes. The resultant was then suspended in an SOC medium (2% Trypton, 0.5% yeast extract, 0.05% NaCl, 10 mM $MgCl_2$, 10 mM $MgSO_4$, and 20 mM glucose), followed by 1 hour of incubation at 37° C. Subsequently, the transformed *Escherichia coli* was cultured at 37° C. overnight on an LB agar medium (1% yeast extract, 0.5% trypton, and 1% NaCl) supplemented with 50 μg/ml ampicillin, thereby obtaining *Escherichia coli* colonies. White clones thought to contain the inserted fragment were selected. The clones were cultured overnight on an LB medium supplemented with 50 μg/ml ampicillin. The plasmid DNA was purified using a GFX (Trademark) Micro Plasmid Prep Kit (produced by Amersham Bioscience). Sequencing reaction was performed using a dye primer cycle sequencing kit (produced by Amersham) and then nucleotide sequence analysis was performed using a fluorescence DNA sequencer (produced by Shimadzu Corporation). In addition, final determination was made when the nucleotide sequences of 3 clones were found to match completely upon the nucleotide sequence analysis thereof (FIG. 7-1 and FIG. 7-2).

Example 12

Analysis of the Zen1 Gene

The Zen1 gene cloned in Example 11 was analyzed using Genetyx-win ver.6 software (produced by Software Development). The number of bases was 1020 bp and the number of amino acid residues was 340 (FIG. 7-1, FIG. 7-2, and SEQ ID NOS: 1 and 2). BLAST search was performed for the nucleotide sequence and the amino acid sequence of the gene, but no clear hits were obtained. The Zen1 gene was thought to be a novel gene.

Example 13

Isolation of Full-Length Zen1 cDNA

Full-length cDNA was isolated by the RACE (rapid amplification of cDNA ends) method. Total RNA was extracted from the mite bodies used in Example 8 using an SV Total RNA isolation kit (produced by Promega). A template for RACE was prepared using a GeneRacer (Trademark) kit (produced by Invitrogen) according to the manual of the kit. Furthermore, based on the Zen1 partial sequences obtained in Example 12, primers for $1^{st}$ PCR and nested PCR were synthesized for amplification of the 5' and the 3' termini (Table 5). Amplification reaction for the 5' and the 3' termini was performed as follows. To 1.0 μL of the template for RACE prepared above, 3.0 μL each of 5' and the 3' primers included in a GeneRacer (Trademark) kit, 1.0 μL of a dNTP mix solution (10 mM each), 5.0 μl of 10×cDNA PCR reaction buffer included in Advantage cDNA Polymerase Mix (produced by CLONTECH), 1.0 μL of Advantage cDNA Polymerase Mix, and 1.0 μL each of the gene-specific primers for the $1^{st}$ PCR synthesized above and adjusted at 10 μM were added. Then the volume of the resulting solution was adjusted to 50.0 μL using sterilized distilled water. Gene amplification was performed using a Touchdown PCR method. The prepared sample solution was subjected to thermal denaturation at 94° C. for 1 minute, 5 cycles of reaction, each of which consisted of 94° C. for 30 seconds and 72° C. for 4 minutes, 5 cycles of reaction, each of which consisted of 94° C. for 30 seconds and 70° C. for 4 minutes, 25 cycles of final reaction, each of which consisted of 94° C. for 30 seconds and 68° C. for 4 minutes, and then storage at 4° C. After completion of the $1^{st}$ PCR, to 1.0 mL each of the 5' and the 3' terminus amplification reaction solutions, 1.0 μL each of 5' primer and 3' primer for Nested PCR included in a GeneRacer (Trademark) kit, 1.0 μL of a dNTP mix solution (10 mM each), 5.0 μl of 10×cDNA PCR reaction buffer included in Advantage cDNA Polymerase Mix (produced by CLONTECH), 1.0 μL of Advantage cDNA Polymerase Mix, and 1.0 μL each of the gene-specific primers for the 1st PCR synthesized above and adjusted at 10 μM were added. Then the volume of the resulting solution was adjusted to 50.0 μL using sterilized distilled water. Gene amplification was performed using the above Touchdown PCR method. The thus obtained amplified fragments of the 5' and 3' termini were confirmed by electrophoresis using 1.0% agarose gel. These fragments were excised and then collected (SUPREC-01 produced by TaKaRa). The fragments were ligated to the cloning site of pGEM-T Easy Vector (produced by Promega) using T4 DNA ligase, thereby transforming host *Escherichia coli* TOP10 (produced by Invitrogen). Specifically, *Escherichia coli* competent cells and a plasmid were mixed and then the mixture was subjected to temperature treatment on ice for 30 minutes, at 42° C. for 30 seconds, and on ice for 2 minutes. The resultant was then suspended in an SOC medium (2% Trypton, 0.5% yeast extract, 0.05% NaCl, 10 mM $MgCl_2$, 10 mM $MgSO_4$, and 20 mM Glucose), followed by 1 hour of incubation at 37° C. Subsequently, the transformed *Escherichia coli* was cultured at 37° C. overnight on an LB agar medium (1% yeast extract, 0.5 trypton, and 1% NaCl) supplemented with 50 μg/ml ampicillin, thereby obtaining *Escherichia coli* colonies. White clones thought to contain the inserted fragments were selected. The clones were cultured overnight on an LB medium supplemented with 50 μg/ml ampicillin. The plasmid DNA was purified using a GFX (Trademark) Micro Plasmid Prep kit (produced by Amersham Bioscience). Sequencing reaction was performed using a dye primer cycle sequencing kit (produced by Amersham) and then nucleotide sequence analysis was performed using a fluorescence DNA sequencer (produced by Shimadzu Corporation). In addition, final determination was made when the nucleotide sequences of 3 clones were found to match completely upon analysis thereof. As a result, the nucleotide sequence of the 5' terminus and that of the 3' terminus of Zen1 could be determined (FIG. 8-1 to FIG. 8-4 and SEQ ID NOS: 34 and 35).

TABLE 5

| Primer name | Sequence | Purpose of use |
|---|---|---|
| Zen1 RS-1 | 5'- AAT TAC AAA CAT GAG TTA GAA -3' | 3' RACE $1^{st}$ PCR |
| Zen1 RS-2 | 5'- GAA TTG TTG ACA ATG TTC AAA -3' | 3' RACE Nested PCR |
| Zen1 RR-1 | 5'- GAT TTC ATC TTT CAA ATC TGA -3' | 5' RACE $1^{st}$ PCR |
| Zen1 RR-2 | 5'- CTT TTC CAA TAC ATC CTG GGC -3' | 5' RACE Nested PCR |

(From the top, SEQ ID NOS: 36, 37, 38, and 39) Primers used in the RACE method and the sequences thereof Example 14

Purification of Recombinant Zen1

Figure 9:
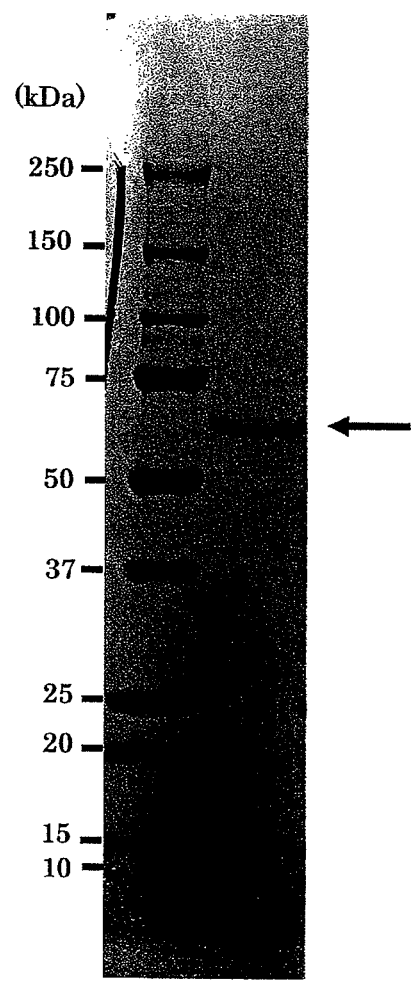
FIG. 9 is a photograph showing the SDS-PAGE result of recombinant Zen1 prepared using *Escherichia coli* and then purified.

Zen1 cDNA obtained in Example 13 to which restriction enzyme BamHI and XhoI sites had been added was amplified by PCR. The amplification product was ligated to the BamHI and XhoI sites of the *Escherichia coli* expression plasmid vector pGEX4T-1 (produced by Amersham Biosciences) using T4-DNA ligase. The *E. coli* TOP10 strain (produced by Invitrogen) was transformed with the thus obtained recombinant plasmid. The transformed strain was cultured at 37° C. overnight on an LB medium containing 100 μg/mL ampicillin. A small amount of the strain was subcultured on a new LB medium until OD at 600 nm reached 1.0. Next, IPTG (isopropyl-1-thio-β-D-galactoside) was added to a final concentration of 1 mM. 3 hours later, cells were harvested and then washed once with PBS (pH 7.4). Cells harvested again were lysed by ultrasonication in PBS (pH 7.4), an insoluble fraction was removed by centrifugation, and then a soluble fraction containing Zen1 fused to glutathione S-transferase (GST) was collected. Subsequently, Zen1 fused to GST was obtained from the soluble fraction using a glutathione sepharose 4B column (produced by Amersham Biosciences). Thrombin (produced by Amersham Biosciences) in an amount 1/100 that of the fusion protein was added to a solution containing a purified fusion product (that is, Zen1 fused to GST), followed by 20 hours of reaction at 22° C. Thus, GST was separated from Zen1. Subsequently, thrombin was removed using Benzamidin Sepharose (produced by Amersham Biosciences) and then a recombinant Zen1 was purified. The thus obtained purified Zen1 showed a single band corresponding to a molecular weight of approximately 60 kDa as confirmed by SDS-PAGE (FIG. 9).

Example 15

Preparation of an Anti-Zen1 Polyclonal Antibody and Analysis of the Reactivity of the Antibody with the Mite Protein Six mice (BALB/c, female, 4-week-old) were immunized 5 times with the recombinant Zen1 purified in Example 14 at 1-week intervals. Subsequently, blood was collected from the mice, the sera were separated, and then the reaction of the IgG antibody was analyzed by ELISA. ELISA was performed as follows. 1.0 μg of the recombinant Zen1 and 4.0 μg of an antigen extracted from *Dermatophagoides farinae* (produced by GREER) were separately immobilized on immunoplates (produced by Nalge Nunc International), followed by 1 hour of blocking at 37° C. using a blocking solution (prepared by adding Tween20 to PBS supplemented with 10% FBS to a final concentration of 0.05%). Each mouse serum sample was diluted 1000-fold with a blocking solution and then allowed to react at room temperature for 1 hour. After washing each immunoplate, an HRP-labeled goat anti-mouse IgG monoclonal antibody (produced by ZYMED) diluted 2000-fold with a blocking solution was caused to react therewith. After washing each immunoplate, 100 μL of an enzyme substrate solution (ABTS solution) was added to each well, followed by 10 minutes of reaction at 37° C. The enzyme reaction was stopped by addition of 100 μL of a 0.32% sodium fluoride solution to each well. The absorbance of each well at 414 nm was measured using an immunoreader (BioRad). After the reaction of IgG to the relevant subject was confirmed by ELISA, the subject was determined to be a polyclonal antibody against Zen1.

Figure 10:
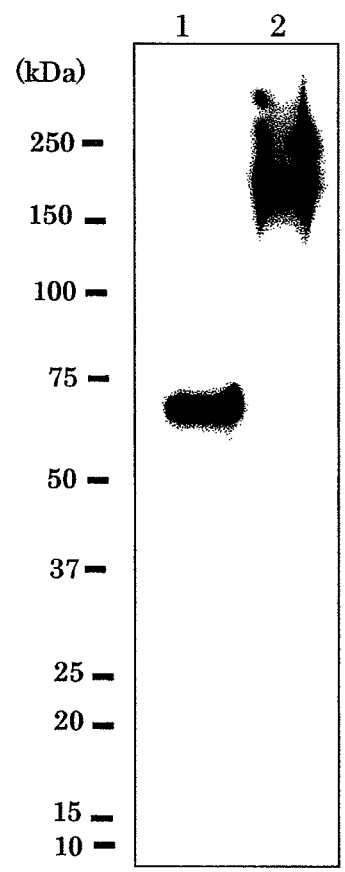
FIG. 10 is a photograph showing the result of a reaction analyzed by Western blotting of an anti-Zen 1 polyclonal antibody. Lane 1 shows the result with regard to a recombinant Zen1 and Lane 2 shows the result with regard to a mite body.

The reactivity of mouse IgG to the polyclonal antibody (the recombinant Zen1) and the same with regard to mite bodies were analyzed by Western blotting. 200 μL of a Laemmli sample buffer (produced by BIO-RAD) was prepared by adding β-mercaptoethanol to a final concentration of 50.0 μL/mL to 100.0 μL of the recombinant Zen1 protein solution adjusted at 50 μg/mL and 100.0 μL of the solution of an antigen extracted from *Dermatophagoides farinae*. After heat treatment at 100° C. for 5 minutes, the resultant was applied to polyacrylamide gel (PAGEL; produced by ATTO) with a gel concentration between 5% and 20%. Thus, electrophoresis was performed. After completion of electrophoresis, the resultant was transferred to a PVDF membrane (Hybond-P; produced by Amersham Biosciences). The membrane was allowed to stand at 4° C. overnight in a blocking solution (PBST (prepared by adding Tween20 to PBS to a final concentration of 0.1%) supplemented with 5% skim milk). The membrane was washed with PBST for 10 minutes. An HRP-labeled goat anti-mouse IgG monoclonal antibody (produced by ZYMED) was diluted 20,000-fold with PBST, and then the diluted solution was added onto the membrane, followed by 2 hours of reaction at room temperature. After 5 instances (10 minutes each) of washing with PBST, the reaction solution of an ECL Plus Western blotting detection system (produced by Amersham Biosciences) was added onto the membrane, followed by 5 minutes of reaction at room temperature. Signals were detected using X-ray film (Hyperfilm ECL; produced by Amersham Biosciences). As a result, a signal indicating the reaction to the recombinant Zen1 with a molecular weight of approximately 60 kDa and a signal indicating the reaction to the natural-type Zen1 with a molecular weight between 150 kDa and 250 kDa were detected (FIG. 10). Accordingly, it was confirmed that the full-length Zen1 cDNA isolated in Example 13 encodes such allergen protein of mite bodies with a molecular weight between 150 kDa and 250 kDa.

Example 16

Analysis of IgE Reactivity of the Recombinant Zen1

Figure 11:
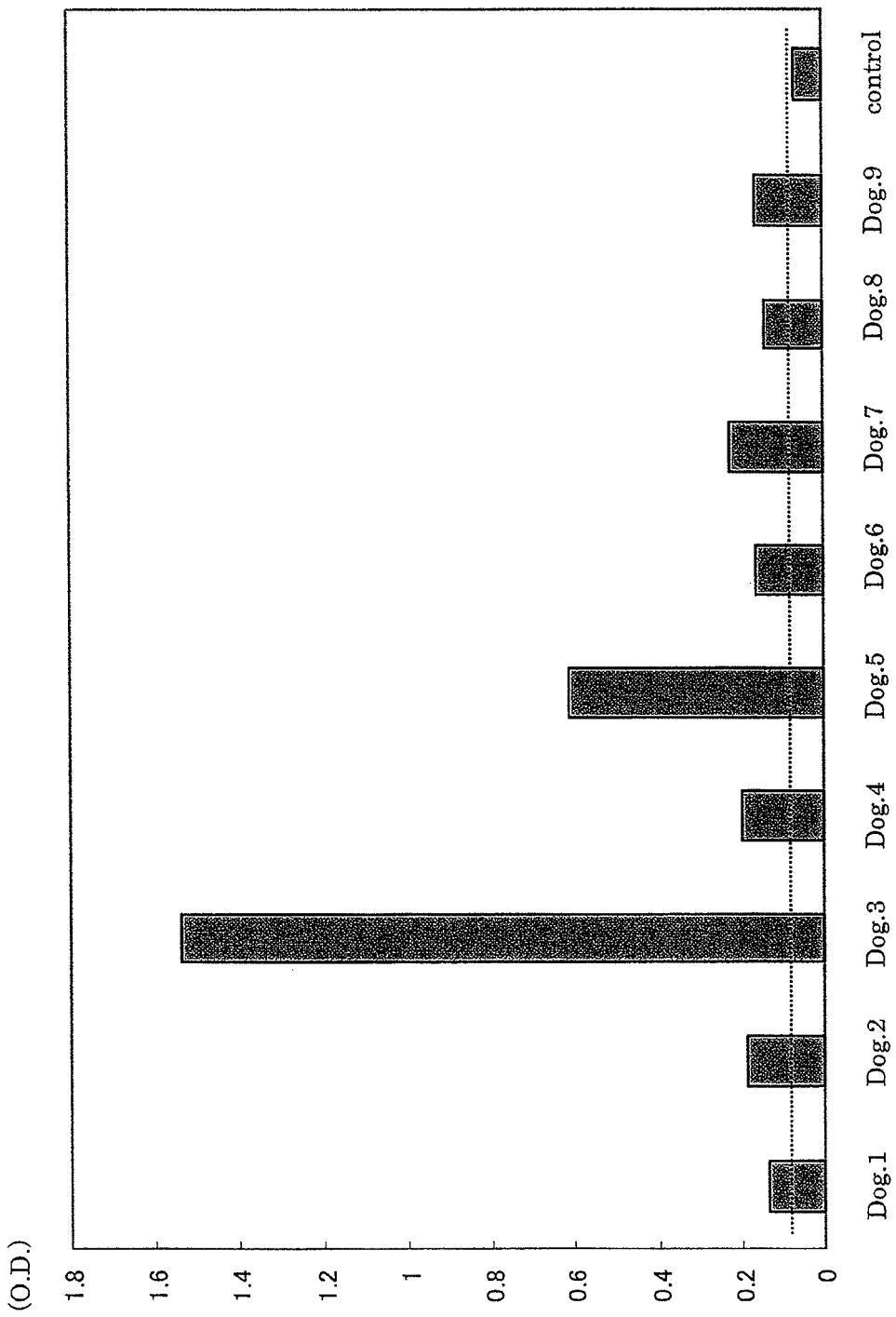
FIG. 11 is a graph showing the reactivity of recombinant Zen1 with IgE as analyzed by ELISA.

The allergenicity of the recombinant Zen1 purified in Example 14 was evaluated by ELISA. 1.0 µg of the recombinant Zen1 was immobilized on an immunoplate (produced by Nalge Nunc International K.K.), followed by blocking at 37° C. for 1 hour with a blocking solution (prepared by adding Tween20 to PBS supplemented with 10% FBS to a final concentration of 0.05%). The sera of nine dogs that tested positive for *Dermatophagoides farinae* (dog sera that tested positive for *Dermatophagoides farinae* as confirmed by an intracutaneous reaction using a *Dermatophagoides farinae* antigen solution (produced by GREER) diluted 50 fold using physiological saline)) were caused to react with a negative control dog serum. Biotin-labeled GST-FcεRIα was added and then a color development reaction was caused to take place by the addition of peroxidase conjugate streptavidin (produced by Jackson Immuno Research) and an enzyme substrate solution (ABTS solution). The enzyme reaction was stopped by the addition of 100 µL of a 0.32% sodium fluoride solution per well. The absorbance of each well at 414 nm was measured using an immunoreader (BioRad). Specifically, the reaction of serum IgE (of nine dogs that had tested positive for mites as confirmed by the intracutaneous reaction of this procedure and of the negative dog (control)) to the recombinant Zen1 was analyzed by an ELISA system using recombinant dog FcεRIα. As a result, values above the value for the negative dog (indicated with a dotted line) were confirmed. Therefore, it was confirmed that the recombinant Zen1 is an allergen protein that reacts with IgE (FIG. 11).

INDUSTRIAL APPLICABILITY

The present invention makes it possible to provide safe and efficient recombinant mite allergens as therapeutic agents or diagnostic agents for mite allergic diseases, which contain no anaphylaxis-inducing impurities.

All publications cited herein are incorporated herein in their entirety. A person skilled in the art would easily understand that various modifications and changes of the present invention are feasible within the technical idea and the scope of the invention as disclosed in the attached claims. The present invention is intended to include such modifications and changes.

What is claimed is:

1. A polypeptide fragment consisting of any one of SEQ ID NOs: 2, 4, 10, 12, or 19.

2. A therapeutic agent for mite allergic diseases, comprising a composition having the polypeptide fragment according to claim 1 as an active ingredient.

3. A diagnostic agent for mite allergic diseases, wherein the diagnostic agent comprises the polypeptide fragment according to claim 1.

4. A polypeptide fragment of SEQ ID NO: 35 comprising any one of SEQ ID NOs: 4, 10, or 19.

5. A polypeptide fragment of SEQ ID NO: 35 comprising SEQ ID NO: 12 wherein the amino acid at position 7 of SEQ ID NO: 12 is glutamic acid.

* * * * *

SEQUENCE LISTING

```
<160> NUMBER OF SEQ ID NOS: 39

<210> SEQ ID NO 1
<211> LENGTH: 1022
<212> TYPE: DNA
<213> ORGANISM: Dermatophagoides farinae
<220> FEATURE:
<221> NAME/KEY: CDS
<222> LOCATION: (1)..(1020)

<400> SEQUENCE: 1 gac gat gta tta aag cag act gag gag cct att aaa agt gcc cag gat      48
Asp Asp Val Leu Lys Gln Thr Glu Glu Pro Ile Lys Ser Ala Gln Asp
  1               5                  10                  15 gta ttg gaa aag ttg ccc gat tca gat ttg aaa gat gaa atc gca gaa      96
Val Leu Glu Lys Leu Pro Asp Ser Asp Leu Lys Asp Glu Ile Ala Glu
             20                  25                  30 aaa ctg gca acc atg aag cat tac aaa cat aag tta gaa aat gca aaa     144
Lys Leu Ala Thr Met Lys His Tyr Lys His Lys Leu Glu Asn Ala Lys
         35                  40                  45 aat cca atc aaa atc gcc cat ttt gaa ttg gaa ttg ttg aca atg ttc     192
Asn Pro Ile Lys Ile Ala His Phe Glu Leu Glu Leu Leu Thr Met Phe
     50                  55                  60 aaa aag ttc caa tca tta ttg aac gaa gct aat gaa att atc aaa tcc     240
Lys Lys Phe Gln Ser Leu Leu Asn Glu Ala Asn Glu Ile Ile Lys Ser
 65                  70                  75                  80 ttg aca acc aca aca acg gaa ccg aca acc cca act cct gaa cca aca     288
Leu Thr Thr Thr Thr Thr Glu Pro Thr Thr Pro Thr Pro Glu Pro Thr
                 85                  90                  95 aca aca act cct gaa ccg act acc aaa acc ccc gaa ccg act acc aaa     336
Thr Thr Thr Pro Glu Pro Thr Thr Lys Thr Pro Glu Pro Thr Thr Lys
            100                 105                 110 aca ccg gaa cca aca aca cca act cct gaa ccg act acc aaa acc ccc     384
Thr Pro Glu Pro Thr Thr Pro Thr Pro Glu Pro Thr Thr Lys Thr Pro
        115                 120                 125
```

| | | | | | | | | | | | | | | | | |
|---|---|---|---|---|---|---|---|---|---|---|---|---|---|---|---|---|
| gaa | ccg | act | acc | aaa | aca | ccg | gaa | cca | aca | aca | cca | act | cca | gaa | ccg | 432 |
| Glu | Pro | Thr | Thr | Lys | Thr | Pro | Glu | Pro | Thr | Thr | Pro | Thr | Pro | Glu | Pro | |
| | | 130 | | | | 135 | | | | 140 | | | | | | |
| act | acc | aaa | aca | ccg | gaa | cca | aca | aca | cca | act | cct | gaa | ccg | act | acc | 480 |
| Thr | Thr | Lys | Thr | Pro | Glu | Pro | Thr | Thr | Pro | Thr | Pro | Glu | Pro | Thr | Thr | |
| 145 | | | | | 150 | | | | | 155 | | | | | 160 | |
| aaa | acc | ccc | gaa | ccg | act | acc | aaa | aca | cct | gaa | cca | tcc | acc | cca | act | 528 |
| Lys | Thr | Pro | Glu | Pro | Thr | Thr | Lys | Thr | Pro | Glu | Pro | Ser | Thr | Pro | Thr | |
| | | | 165 | | | | | 170 | | | | | 175 | | | |
| ccg | gac | cgc | tac | caa | aac | ccc | cga | ccg | cta | cca | aaa | cac | cgg | acc | atc | 576 |
| Pro | Asp | Arg | Tyr | Gln | Asn | Pro | Arg | Pro | Leu | Pro | Lys | His | Arg | Thr | Ile | |
| | | | 180 | | | | | 185 | | | | | 190 | | | |
| cac | ccc | aac | tcc | gga | ccg | act | acc | aaa | aca | cct | gaa | cca | tcc | act | cca | 624 |
| His | Pro | Asn | Ser | Gly | Pro | Thr | Thr | Lys | Thr | Pro | Glu | Pro | Ser | Thr | Pro | |
| | | | 195 | | | | | 200 | | | | | 205 | | | |
| act | ccg | gaa | ccg | act | acc | aaa | acc | ccc | gaa | ccg | act | acc | aaa | aca | ccg | 672 |
| Thr | Pro | Glu | Pro | Thr | Thr | Lys | Thr | Pro | Glu | Pro | Thr | Thr | Lys | Thr | Pro | |
| | | | 210 | | | | | 215 | | | | | 220 | | | |
| gaa | cca | tca | acc | cca | act | ccg | gaa | ccg | act | acc | aaa | aca | ccg | gaa | cca | 720 |
| Glu | Pro | Ser | Thr | Pro | Thr | Pro | Glu | Pro | Thr | Thr | Lys | Thr | Pro | Glu | Pro | |
| 225 | | | | | 230 | | | | | 235 | | | | | 240 | |
| tca | acc | cca | act | ccg | gaa | ccg | act | acc | aaa | aca | ccg | gaa | cca | tca | acg | 768 |
| Ser | Thr | Pro | Thr | Pro | Glu | Pro | Thr | Thr | Lys | Thr | Pro | Glu | Pro | Ser | Thr | |
| | | | | 245 | | | | | 250 | | | | | 255 | | |
| act | aag | aaa | cct | aat | cgg | gat | gat | gtt | ttg | aaa | caa | gct | gaa | gag | ctt | 816 |
| Thr | Lys | Lys | Pro | Asn | Arg | Asp | Asp | Val | Leu | Lys | Gln | Ala | Glu | Glu | Leu | |
| | | | 260 | | | | | 265 | | | | | 270 | | | |
| att | aaa | aga | gcc | gag | gat | gta | ttt | gaa | aag | ttg | ccc | gat | tca | gat | ttg | 864 |
| Ile | Lys | Arg | Ala | Glu | Asp | Val | Phe | Glu | Lys | Leu | Pro | Asp | Ser | Asp | Leu | |
| | | | 275 | | | | | 280 | | | | | 285 | | | |
| aaa | aat | gaa | atc | gca | gaa | aaa | ctg | gca | acc | atg | aag | aat | tac | aaa | cat | 912 |
| Lys | Asn | Glu | Ile | Ala | Glu | Lys | Leu | Ala | Thr | Met | Lys | Asn | Tyr | Lys | His | |
| | | 290 | | | | | 295 | | | | | 300 | | | | |
| gag | tta | gaa | aat | gca | aaa | aat | cca | atc | aaa | atc | gcc | cat | ctt | gaa | tcg | 960 |
| Glu | Leu | Glu | Asn | Ala | Lys | Asn | Pro | Ile | Lys | Ile | Ala | His | Leu | Glu | Ser | |
| 305 | | | | | 310 | | | | | 315 | | | | | 320 | |
| gaa | ttg | ttg | aca | atg | ttc | aaa | atg | ttc | caa | tca | ttg | tta | aat | gaa | gcc | 1008 |
| Glu | Leu | Leu | Thr | Met | Phe | Lys | Met | Phe | Gln | Ser | Leu | Leu | Asn | Glu | Ala | |
| | | | | 325 | | | | | 330 | | | | | 335 | | |
| aac | gaa | ctc | ctg | aa | | | | | | | | | | | | 1022 |
| Asn | Glu | Leu | Leu | | | | | | | | | | | | | |
| | | | 340 | | | | | | | | | | | | | |

<210> SEQ ID NO 2
<211> LENGTH: 340
<212> TYPE: PRT
<213> ORGANISM: Dermatophagoides farinae

<400> SEQUENCE: 2

Asp Asp Val Leu Lys Gln Thr Glu Glu Pro Ile Lys Ser Ala Gln Asp
 1               5                  10                  15

Val Leu Glu Lys Leu Pro Asp Ser Asp Leu Lys Asp Glu Ile Ala Glu
             20                  25                  30

Lys Leu Ala Thr Met Lys His Tyr Lys His Lys Leu Glu Asn Ala Lys
         35                  40                  45

Asn Pro Ile Lys Ile Ala His Phe Glu Leu Glu Leu Leu Thr Met Phe
     50                  55                  60

Lys Lys Phe Gln Ser Leu Leu Asn Glu Ala Asn Glu Ile Ile Lys Ser
 65                  70                  75                  80

```
Leu Thr Thr Thr Thr Thr Glu Pro Thr Thr Pro Thr Glu Pro Thr
                85                  90                  95
Thr Thr Thr Pro Glu Pro Thr Thr Lys Thr Pro Glu Pro Thr Thr Lys
            100                 105                 110
Thr Pro Glu Pro Thr Thr Pro Thr Pro Glu Pro Thr Thr Lys Thr Pro
            115                 120                 125
Glu Pro Thr Thr Lys Thr Pro Glu Pro Thr Thr Pro Thr Pro Glu Pro
        130                 135                 140
Thr Thr Lys Thr Pro Glu Pro Thr Thr Pro Thr Pro Glu Pro Thr Thr
145                 150                 155                 160
Lys Thr Pro Glu Pro Thr Thr Lys Thr Pro Glu Pro Ser Thr Pro Thr
                165                 170                 175
Pro Asp Arg Tyr Gln Asn Pro Arg Pro Leu Pro Lys His Arg Thr Ile
            180                 185                 190
His Pro Asn Ser Gly Pro Thr Thr Lys Thr Pro Glu Pro Ser Thr Pro
            195                 200                 205
Thr Pro Glu Pro Thr Thr Lys Thr Pro Glu Pro Thr Thr Lys Thr Pro
        210                 215                 220
Glu Pro Ser Thr Pro Thr Pro Glu Pro Thr Thr Lys Thr Pro Glu Pro
225                 230                 235                 240
Ser Thr Pro Thr Pro Glu Pro Thr Thr Lys Thr Pro Glu Pro Ser Thr
                245                 250                 255
Thr Lys Lys Pro Asn Arg Asp Asp Val Leu Lys Gln Ala Glu Leu
            260                 265                 270
Ile Lys Arg Ala Glu Asp Val Phe Glu Lys Leu Pro Asp Ser Asp Leu
        275                 280                 285
Lys Asn Glu Ile Ala Glu Lys Leu Ala Thr Met Lys Asn Tyr Lys His
290                 295                 300
Glu Leu Glu Asn Ala Lys Asn Pro Ile Lys Ile Ala His Leu Glu Ser
305                 310                 315                 320
Glu Leu Leu Thr Met Phe Lys Met Phe Gln Ser Leu Leu Asn Glu Ala
            325                 330                 335
Asn Glu Leu Leu
        340

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Lys Ser Leu Leu Asn Glu Ala Asn Glu Leu Leu Lys
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Gln Asp Val Leu Glu Lys
1               5
```

-continued

```
<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Met Gln Ser Leu Leu Asn Glu Ala Asp Glu Leu Leu Arg
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Pro Asp Ser Asp Leu Lys Asp Glu Leu Ala Lys
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Pro Asp Ser Asp Leu Lys Asn Glu Leu Ala Glu Lys
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Tyr Asn Phe His Leu Glu Ala Tyr
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ala His Phe Leu Glu Leu Glu
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

```
Ile Ala His Phe Glu Leu Glu
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Phe Gln Ser Leu Leu Asn Glu Ala Asn
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Glu or Thr

<400> SEQUENCE: 12

Ile Ala His Leu Glu Ser Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Asn or Glu

<400> SEQUENCE: 13

Lys Phe Gln Ser Leu Leu Xaa Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid

<400> SEQUENCE: 14

Asp Ala Gln Leu Glu Xaa Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Ser Ala Gln Asp Val Ser Leu
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Asn Glu Met Asn Glu
 1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Phe Gln Ser Leu Leu Asn Lys Ala Asp Phe Asp
 1               5                  10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: variable amino acid

<400> SEQUENCE: 18

Asp Leu Ala Arg Asp Val Xaa Leu
 1               5

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Asn Arg Asp Asp Val Leu Lys Gln Thr Glu Glu
 1               5                  10

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: a, c, g, t, unknown or other
<220> FEATURE:
<221> NAME/KEY: modified_base
<222> LOCATION: (21)
```

-continued

<223> OTHER INFORMATION: a, c, g, t, unknown or other

<400> SEQUENCE: 20
gaygaygtnt traarcarac ngargar                                    27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: a, c, g, t, unknown or other
<220> FEATURE:
<221> NAME/KEY: modified_base
<222> LOCATION: (11)
<223> OTHER INFORMATION: a, c, g, t, unknown or other
<220> FEATURE:
<221> NAME/KEY: modified_base
<222> LOCATION: (21)
<223> OTHER INFORMATION: a, c, g, t, unknown or other

<400> SEQUENCE: 21
gaygaygtnc tnaarcarac ngargar                                    27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)
<223> OTHER INFORMATION: a, c, g, t, unknown or other

<400> SEQUENCE: 22
rttraaraar tcyttngcrt cyttraa                                    27

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)
<223> OTHER INFORMATION: a, c, g, t, unknown or other
<220> FEATURE:
<221> NAME/KEY: modified_base
<222> LOCATION: (16)
<223> OTHER INFORMATION: a, c, g, t, unknown or other

<400> SEQUENCE: 23
rttnagraar tcyttngcrt cytt                                       24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)

```
<223> OTHER INFORMATION: a, c, g, t, unknown or other
<220> FEATURE:
<221> NAME/KEY: modified_base
<222> LOCATION: (16)
<223> OTHER INFORMATION: a, c, g, t, unknown or other

<400> SEQUENCE: 24
rttraanagr tcyttngcrt cytt                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)
<223> OTHER INFORMATION: a, c, g, t, unknown or other
<220> FEATURE:
<221> NAME/KEY: modified_base
<222> LOCATION: (7)
<223> OTHER INFORMATION: a, c, g, t, unknown or other
<220> FEATURE:
<221> NAME/KEY: modified_base
<222> LOCATION: (16)
<223> OTHER INFORMATION: a, c, g, t, unknown or other

<400> SEQUENCE: 25
rttnagnagr tcyttngcrt cytt                                          24

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (10)
<223> OTHER INFORMATION: a, c, g, t, unknown or other
<220> FEATURE:
<221> NAME/KEY: modified_base
<222> LOCATION: (19)
<223> OTHER INFORMATION: a, c, g, t, unknown or other

<400> SEQUENCE: 26
rttrtcraan acytcrtgng c                                             21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)
<223> OTHER INFORMATION: a, c, g, t, unknown or other
<220> FEATURE:
<221> NAME/KEY: modified_base
<222> LOCATION: (10)
<223> OTHER INFORMATION: a, c, g, t, unknown or other
<220> FEATURE:
<221> NAME/KEY: modified_base
<222> LOCATION: (19)
<223> OTHER INFORMATION: a, c, g, t, unknown or other

<400> SEQUENCE: 27
rttrtcnagn acytcrtgng c                                             21
```

```
<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)
<223> OTHER INFORMATION: a, c, g, t, unknown or other

<400> SEQUENCE: 28
rttrtcngcr aartcyttrt t                                            21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)
<223> OTHER INFORMATION: a, c, g, t, unknown or other
<220> FEATURE:
<221> NAME/KEY: modified_base
<222> LOCATION: (10)
<223> OTHER INFORMATION: a, c, g, t, unknown or other

<400> SEQUENCE: 29
rttrtcngcn agrtcyttrt t                                            21

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)
<223> OTHER INFORMATION: a, c, g, t, unknown or other

<400> SEQUENCE: 30
rttngcraar tcytcrttra aytc                                         24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)
<223> OTHER INFORMATION: a, c, g, t, unknown or other
<220> FEATURE:
<221> NAME/KEY: modified_base
<222> LOCATION: (7)
<223> OTHER INFORMATION: a, c, g, t, unknown or other

<400> SEQUENCE: 31
rttngcnagr tcytcrttra aytc                                         24

<210> SEQ ID NO 32
<211> LENGTH: 24
```

-continued

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)
<223> OTHER INFORMATION: a, c, g, t, unknown or other
<220> FEATURE:
<221> NAME/KEY: modified_base
<222> LOCATION: (19)
<223> OTHER INFORMATION: a, c, g, t, unknown or other

<400> SEQUENCE: 32
rttngcraar tcytcrttna gytc                                           24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)
<223> OTHER INFORMATION: a, c, g, t, unknown or other
<220> FEATURE:
<221> NAME/KEY: modified_base
<222> LOCATION: (7)
<223> OTHER INFORMATION: a, c, g, t, unknown or other
<220> FEATURE:
<221> NAME/KEY: modified_base
<222> LOCATION: (19)
<223> OTHER INFORMATION: a, c, g, t, unknown or other

<400> SEQUENCE: 33
rttngcnagr tcytcrttna gytc                                           24

<210> SEQ ID NO 34
<211> LENGTH: 1518
<212> TYPE: DNA
<213> ORGANISM: Dermatophagoides farinae
<220> FEATURE:
<221> NAME/KEY: CDS
<222> LOCATION: (1)..(1515)

<400> SEQUENCE: 34 atg aaa tta acc gct aca tta ctg ttg att cta aca ttg agt tgg gca      48
Met Lys Leu Thr Ala Thr Leu Leu Leu Ile Leu Thr Leu Ser Trp Ala
 1               5                  10                  15 ggt att ttc gtt gat gca aat cca cga ttc aaa cgt gat aat cgg gat      96
Gly Ile Phe Val Asp Ala Asn Pro Arg Phe Lys Arg Asp Asn Arg Asp
             20                  25                  30 gat gtt ttg aaa caa act gaa gag ctt att aaa agt gcc cag gat gta     144
Asp Val Leu Lys Gln Thr Glu Glu Leu Ile Lys Ser Ala Gln Asp Val
         35                  40                  45 ttg gaa aag ttg ccc gat tca gat ttg aaa gat gaa atc gca gaa aaa     192
Leu Glu Lys Leu Pro Asp Ser Asp Leu Lys Asp Glu Ile Ala Glu Lys
     50                  55                  60 ctg gca acc atg aag cat tac aaa cat aag tta gaa aat gca aaa aat     240
Leu Ala Thr Met Lys His Tyr Lys His Lys Leu Glu Asn Ala Lys Asn
 65                  70                  75                  80 cca atc aaa atc gcc cat ttt gaa ttg gaa ttg ttg aca atg ttc aaa     288
Pro Ile Lys Ile Ala His Phe Glu Leu Glu Leu Leu Thr Met Phe Lys
                 85                  90                  95 aag ttc caa tca tta ttg aac gaa gct aat gaa att atc aaa tcc ttg     336
Lys Phe Gln Ser Leu Leu Asn Glu Ala Asn Glu Ile Ile Lys Ser Leu
```

-continued

```
                100                 105                 110
aca acc aca aca acg gaa ccg aca acc cca act cct gaa cca aca aca        384
Thr Thr Thr Thr Thr Glu Pro Thr Thr Pro Thr Pro Glu Pro Thr Thr
            115                 120                 125 aca act cct gaa ccg act acc aaa acc ccc gaa ccg act acc aaa aca        432
Thr Thr Pro Glu Pro Thr Thr Lys Thr Pro Glu Pro Thr Thr Lys Thr
        130                 135                 140 ccg gaa cca aca aca cca act cct gaa ccg act acc aaa acc ccc gaa        480
Pro Glu Pro Thr Thr Pro Thr Pro Glu Pro Thr Thr Lys Thr Pro Glu
145                 150                 155                 160 ccg act acc aaa aca ccg gaa cca aca aca cca act cca gaa ccg act        528
Pro Thr Thr Lys Thr Pro Glu Pro Thr Thr Pro Thr Pro Glu Pro Thr
            165                 170                 175 acc aaa aca ccg gaa cca aca aca cca act cct gaa ccg act acc aaa        576
Thr Lys Thr Pro Glu Pro Thr Thr Pro Thr Pro Glu Pro Thr Thr Lys
        180                 185                 190 acc ccc gaa ccg act acc aaa aca cct gaa cca tcc acc cca act ccg        624
Thr Pro Glu Pro Thr Thr Lys Thr Pro Glu Pro Ser Thr Pro Thr Pro
    195                 200                 205 gac cgc tac caa aac ccc cga ccg cta cca aaa cac cgg acc atc cac        672
Asp Arg Tyr Gln Asn Pro Arg Pro Leu Pro Lys His Arg Thr Ile His
210                 215                 220 ccc aac tcc gga ccg act acc aaa aca cct gaa cca tcc act cca act        720
Pro Asn Ser Gly Pro Thr Thr Lys Thr Pro Glu Pro Ser Thr Pro Thr
225                 230                 235                 240 ccg gaa ccg act acc aaa acc ccc gaa ccg act acc aaa aca ccg gaa        768
Pro Glu Pro Thr Thr Lys Thr Pro Glu Pro Thr Thr Lys Thr Pro Glu
            245                 250                 255 cca tca acc cca act ccg gaa ccg act acc aaa aca ccg gaa cca tca        816
Pro Ser Thr Pro Thr Pro Glu Pro Thr Thr Lys Thr Pro Glu Pro Ser
        260                 265                 270 acc cca act ccg gaa ccg act acc aaa aca ccg gaa cca tca acg act        864
Thr Pro Thr Pro Glu Pro Thr Thr Lys Thr Pro Glu Pro Ser Thr Thr
    275                 280                 285 aag aaa cct aat cgg gat gat gtt ttg aaa caa gct gaa gag ctt att        912
Lys Lys Pro Asn Arg Asp Asp Val Leu Lys Gln Ala Glu Glu Leu Ile
290                 295                 300 aaa aga gcc gag gat gta ttt gaa aag ttg ccc gat tca gat ttg aaa        960
Lys Arg Ala Glu Asp Val Phe Glu Lys Leu Pro Asp Ser Asp Leu Lys
305                 310                 315                 320 aat gaa atc gca gaa aaa ctg gca acc atg aag aat tac aaa cat gag       1008
Asn Glu Ile Ala Glu Lys Leu Ala Thr Met Lys Asn Tyr Lys His Glu
            325                 330                 335 tta gaa aat gca aaa aat cca atc aaa atc gcc cat ctt gaa tcg gaa       1056
Leu Glu Asn Ala Lys Asn Pro Ile Lys Ile Ala His Leu Glu Ser Glu
        340                 345                 350 ttg ttg aca atg ttc aaa atg ttc caa tca ttg ttg aac gaa gct gat       1104
Leu Leu Thr Met Phe Lys Met Phe Gln Ser Leu Leu Asn Glu Ala Asp
    355                 360                 365 gaa att atc aga tcc ttg aca act acg gaa ccg aca aca ttg aat            1152
Glu Ile Ile Arg Ser Leu Thr Thr Thr Glu Pro Thr Thr Leu Asn
370                 375                 380 agc acc act ccg gaa ccg aca aca ttg aat agc acc act ccg gaa ccg       1200
Ser Thr Thr Pro Glu Pro Thr Thr Leu Asn Ser Thr Thr Pro Glu Pro
385                 390                 395                 400 aca aca ttg aat agc acc act ccg gaa ccg aca aca ttg aat agc acc       1248
Thr Thr Leu Asn Ser Thr Thr Pro Glu Pro Thr Thr Leu Asn Ser Thr
            405                 410                 415 act ccg gaa ccg aca aca ttg aat agc acc act ccg gga ccg aca aca       1296
Thr Pro Glu Pro Thr Thr Leu Asn Ser Thr Thr Pro Gly Pro Thr Thr
```

```
                      420                425                430
ttg aat agc acc act ccg gaa ccg aca aca ttg aat agc acc act ccg    1344
Leu Asn Ser Thr Thr Pro Glu Pro Thr Thr Leu Asn Ser Thr Thr Pro
        435                 440                 445 gaa ccg aca aca ttg aat agc acc act ccg gaa ccg aca aca tcg aat    1392
Glu Pro Thr Thr Leu Asn Ser Thr Thr Pro Glu Pro Thr Thr Ser Asn
450                 455                 460 agc acc act tca gaa cca acg aat tca atc aat aga aaa aca agt gaa    1440
Ser Thr Thr Ser Glu Pro Thr Asn Ser Ile Asn Arg Lys Thr Ser Glu
465                 470                 475                 480 ttt cat tct tat ccg att ggt tcc ata aga ttc gaa tca gat tca ata    1488
Phe His Ser Tyr Pro Ile Gly Ser Ile Arg Phe Glu Ser Asp Ser Ile
            485                 490                 495 ttt tct aaa cat ttt att ctt ttg att tga                            1518
Phe Ser Lys His Phe Ile Leu Leu Ile
                500                 505

<210> SEQ ID NO 35
<211> LENGTH: 505
<212> TYPE: PRT
<213> ORGANISM: Dermatophagoides farinae

<400> SEQUENCE: 35

Met Lys Leu Thr Ala Thr Leu Leu Ile Leu Thr Leu Ser Trp Ala
1               5                   10                  15

Gly Ile Phe Val Asp Ala Asn Pro Arg Phe Lys Arg Asp Asn Arg Asp
                20                  25                  30

Asp Val Leu Lys Gln Thr Glu Glu Leu Ile Lys Ser Ala Gln Asp Val
            35                  40                  45

Leu Glu Lys Leu Pro Asp Ser Asp Leu Lys Asp Glu Ile Ala Glu Lys
        50                  55                  60

Leu Ala Thr Met Lys His Tyr Lys His Lys Leu Glu Asn Ala Lys Asn
65                  70                  75                  80

Pro Ile Lys Ile Ala His Phe Glu Leu Glu Leu Leu Thr Met Phe Lys
                85                  90                  95

Lys Phe Gln Ser Leu Leu Asn Glu Ala Asn Glu Ile Ile Lys Ser Leu
            100                 105                 110

Thr Thr Thr Thr Thr Glu Pro Thr Pro Thr Pro Glu Pro Thr Thr
        115                 120                 125

Thr Thr Pro Glu Pro Thr Thr Lys Thr Pro Glu Pro Thr Thr Lys Thr
130                 135                 140

Pro Glu Pro Thr Thr Pro Thr Pro Glu Pro Thr Thr Lys Thr Pro Glu
145                 150                 155                 160

Pro Thr Thr Lys Thr Pro Glu Pro Thr Thr Pro Thr Pro Glu Pro Thr
                165                 170                 175

Thr Lys Thr Pro Glu Pro Thr Thr Pro Thr Pro Glu Pro Thr Thr Lys
            180                 185                 190

Thr Pro Glu Pro Thr Thr Lys Thr Pro Glu Pro Ser Thr Pro Thr Pro
        195                 200                 205

Asp Arg Tyr Gln Asn Pro Arg Pro Leu Pro Lys His Arg Thr Ile His
210                 215                 220

Pro Asn Ser Gly Pro Thr Thr Lys Thr Pro Glu Pro Ser Thr Pro Thr
225                 230                 235                 240

Pro Glu Pro Thr Thr Lys Thr Pro Glu Pro Thr Thr Lys Thr Pro Glu
                245                 250                 255

Pro Ser Thr Pro Thr Pro Glu Pro Thr Thr Lys Thr Pro Glu Pro Ser
            260                 265                 270
```

```
Thr Pro Thr Pro Glu Pro Thr Thr Lys Thr Pro Glu Pro Ser Thr Thr
            275                 280                 285

Lys Lys Pro Asn Arg Asp Asp Val Leu Lys Gln Ala Glu Glu Leu Ile
            290                 295                 300

Lys Arg Ala Glu Asp Val Phe Glu Lys Leu Pro Asp Ser Asp Leu Lys
305                 310                 315                 320

Asn Glu Ile Ala Glu Lys Leu Ala Thr Met Lys Asn Tyr Lys His Glu
                325                 330                 335

Leu Glu Asn Ala Lys Asn Pro Ile Lys Ile Ala His Leu Glu Ser Glu
            340                 345                 350

Leu Leu Thr Met Phe Lys Met Phe Gln Ser Leu Leu Asn Glu Ala Asp
            355                 360                 365

Glu Ile Ile Arg Ser Leu Thr Thr Thr Glu Pro Thr Thr Leu Asn
            370                 375                 380

Ser Thr Thr Pro Glu Pro Thr Thr Leu Asn Ser Thr Thr Pro Glu Pro
385                 390                 395                 400

Thr Thr Leu Asn Ser Thr Thr Pro Glu Pro Thr Thr Leu Asn Ser Thr
                405                 410                 415

Thr Pro Glu Pro Thr Thr Leu Asn Ser Thr Thr Pro Gly Pro Thr Thr
            420                 425                 430

Leu Asn Ser Thr Thr Pro Glu Pro Thr Thr Leu Asn Ser Thr Thr Pro
            435                 440                 445

Glu Pro Thr Thr Leu Asn Ser Thr Thr Pro Glu Pro Thr Thr Ser Asn
450                 455                 460

Ser Thr Thr Ser Glu Pro Thr Asn Ser Ile Asn Arg Lys Thr Ser Glu
465                 470                 475                 480

Phe His Ser Tyr Pro Ile Gly Ser Ile Arg Phe Glu Ser Asp Ser Ile
                485                 490                 495

Phe Ser Lys His Phe Ile Leu Leu Ile
            500                 505

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aattacaaac atgagttaga a                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaattgttga caatgttcaa a                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 38
gatttcatct ttcaaatctg a                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cttttccaat acatcctggg c                                              21
```